(12) United States Patent
Griffioen et al.

(10) Patent No.: US 11,548,881 B2
(45) Date of Patent: Jan. 10, 2023

(54) COMPOUNDS FOR THE TREATMENT OF EPILEPSY, NEURODEGENERATIVE DISORDERS AND OTHER CNS DISORDERS

(71) Applicants: reMYND N.V., Leuven (BE); Katholieke Universiteit Leuven, Leuven (BE)

(72) Inventors: Johan Gerard Griffioen, Kessel-Lo (BE); Katrien Princen, Heverlee (BE); Tom Francois L. Van Dooren, Koningshooikt (BE); Arnaud Didier Marie Marchand, Bierbeek (BE); Amuri Kilonda, Boutersem (BE); Sara Allasia, Mechelen (BE); Patrick Chaltin, Zetrud-Lumay (BE)

(73) Assignees: reMYND N.V., Leuven (BE); Katholieke Universiteit Leuven, Leuven (BE)

( * ) Notice: Subject to any disclaimer, the term of this patent is extended or adjusted under 35 U.S.C. 154(b) by 117 days.

(21) Appl. No.: 16/612,096

(22) PCT Filed: May 11, 2018

(86) PCT No.: PCT/EP2018/062199
§ 371 (c)(1),
(2) Date: Nov. 8, 2019

(87) PCT Pub. No.: WO2018/206760
PCT Pub. Date: Nov. 15, 2018

(65) Prior Publication Data
US 2020/0095238 A1 Mar. 26, 2020

(30) Foreign Application Priority Data
May 11, 2017 (EP) .................... 17170674

(51) Int. Cl.
*C07D 413/12* (2006.01)
*A61P 25/28* (2006.01)

(52) U.S. Cl.
CPC ............ *C07D 413/12* (2013.01); *A61P 25/28* (2018.01)

(58) Field of Classification Search
CPC ................ C07D 413/12; A61P 25/28
See application file for complete search history.

(56) References Cited

U.S. PATENT DOCUMENTS

| | | | |
|---|---|---|---|
| 4,997,834 A | 3/1991 | Muro et al. | |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 8,618,138 B2* | 12/2013 | Griffioen ............ | A61K 31/4192 514/339 |

FOREIGN PATENT DOCUMENTS

| | | |
|---|---|---|
| EP | 0370498 | 5/1990 |
| EP | 0721331 | 12/2001 |
| WO | WO 95/09615 | 4/1995 |
| WO | WO 99/33792 | 7/1999 |
| WO | WO 99/33793 | 7/1999 |
| WO | WO 99/33795 | 7/1999 |
| WO | WO 99/33815 | 7/1999 |
| WO | WO 2010/142801 | 12/2010 |
| WO | WO 2011/084642 | 7/2011 |
| WO | WO 2014/210159 | 12/2014 |

OTHER PUBLICATIONS

Hyman, A glimmer of light for neuropsychiatric disorders, 2008, Nature, vol. 455, p. 890-893 (Year: 2008).*
Almarsson et al., "Crystal engineering of the composition of pharmaceutical phases. Do pharmaceutical co-crystals represent a new path to improved medicines?" Chem Commun., (2004) 17:1889-1896.
Britain, H.G. (ed.), Polymorphism in Pharmaceutical Solids (2$^{nd}$ Ed., 1995, Marcel Dekker, New York, New York).
Brunton (ed.), The Pharmacological Basis of Therapeutics (11th Ed, 1992, McGraw-Hill, Int. Ed.).

(Continued)

*Primary Examiner* — Kamal A Saeed
(74) *Attorney, Agent, or Firm* — Knobbe Martens Olson & Bear LLP

(57) ABSTRACT

The present invention relates to a compound of formula (I) or a tautomer thereof, wherein $R^1$, $R^2$, $R^3$, $R^4$ and $R^5$, have the same meaning as that defined in the claims and the description. The present invention also relates to compositions, in particular pharmaceuticals, comprising such compounds, and to uses of such compounds and compositions for the prevention and/or treatment of epilepsy and/or neurodegenerative diseases.

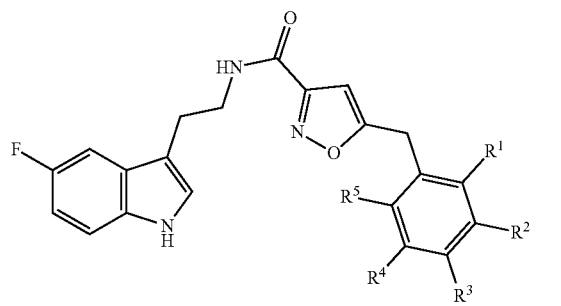

12 Claims, 6 Drawing Sheets

(56) References Cited

OTHER PUBLICATIONS

Dewachter et al., "Aging Increased Amyloid Peptide and Caused Amyloid Plaques in Brain of Old APP/V717I Transgenic Mice by a Different Mechanism than Mutant Presenilin1" The Journal of Neuroscience (2000) 20(17):6452-6458.
Dietrich et al., "Structural and functional changes during epileptogenesis in the mouse model of Medial Temporal Lobe Epilepsy" Conf Proc IEEE Eng Med Biol Soc., (Aug. 2016):4005-4008.
Gröticke et al., "Behavioral alterations in a mouse model of temporal lobe epilepsy induced by intrahippocampal injection of kainate" Experimental Neurology (2008) 213(1):71-83.
Haleblian, J.K., "Characterization of Habits and Crystalline Modification of Solids and Their Pharmaceutical Applications" J Pharm Sci,, (1975) 64(8):1269-1288.
Hartshorne et al., Crystals and the Polarizing Microscope ($4^{th}$ Ed., 1970, Edward Arnold, Elsevier, New York), Summary Only.
Klein, W.L., "Aβ toxicity in Alzheimer's disease: globular oligomers (ADDLs) as new vaccine and drug targets" Neurochemistry International (2002) 41(5):345-52.
Moechars et al., "Early Phenotypic Changes in Transgenic Mice That Overexpress Different Mutants of Amyloid Precursor Protein in Brain" J. Biol. Chem., (1999) 274(10):6483-6492.
Racine, R.J., "Modification of seizure activity by electrical stimulation: Cortical areas" Electroencephalogr Clin Neurophysiol., (1975) 38(1):1-12.
Schlager et al., "Bicaudal D Family Adaptor Proteins Control the Velocity of Dynein-Based Movements" Cell Reports (2014) 8(5):1248-56.
Stahl and Wermuth (eds), Handbook of Pharmaceutical Salts: Properties, Selection, and Use (Wiley-VCH, 2002).
International Search Report and Written Opinion dated Sep. 3, 2018 for PCT Application No. PCT/EP2018/062199, filed May 11, 2018.
International Preliminary Report on Patentability dated Nov. 21, 2019 for PCT Application No. PCT/EP2018/062199, filed May 11, 2018.
Demirel et al., "Total tau and Phosphorylated Tau Protein Serum Levels in Patients with Schizophrenia Compared with Controls" Psychiatr Q (2017) 88:921-928.
Di et al., "Abnormal tau induces cognitive impairment through two different mechanisms: synaptic dysfunction and neuronal loss" Nature Scientific Reports (2016) 6:20833.
Gomperts et al., "Tau PET imaging in the Lewy body diseases" JAMA Neurol (2016) 73(11):1334-1341.
Haggerty et al., "Hyperphosphorylated tau in an α-synuclein overexpressing transgenic model of Parkinson's disease" Eur J Neurosci (2011) 33(9):1598-1610.
Jakobsson et al., "CACNA1C polymorphism and altered phosphorylation of tau in bipolar disorder" The British Journal of Psychiatry (2016) 208:195-196.
Lavretsky et al., "Depression and Anxiety Symptoms Are Associated with Cerebral FDDNP-PET Binding in Middle-Aged and Older Non-Demented Adults" Am J Geriatr Psychiatry (2009) 17(6):493-502.
Murray et al., "Hyperphosphrylated Tau is Elevated in Alzheimer's Disease with Psychosis" J Alzheimers Dis (2014) 39(4):759-773.
Reichling et al., "Pain and Death: Neurodegenerative Disease Mechanisms in the Nociceptor" Ann Neurol (2011) 69:13-21.
Riku et al., "Extensive aggregation of α-synuclein and tau in juvenile-onset neuroaxonal dystrophy: an autopsied individual with a novel mutation in the PLA2G6 gene-splicing site" Acta Neuropathologica Communications (2013) 1:12.
Ryoo et al., "DYRK1A-mediated Hyperphosphorylation of Tau A Functional Link Between Down Syndrome and Alzheimer Disease" The Journal of British Chemistry (2007) 282(48):34850-34857.
Saito et al., "Widespread expression of a-synuclein and t immunoreactivity in Hallervorden-Spatz syndrome with protracted clinical course" Journal of the Neurological Sciences (2000) 177:48-59.
Sanchez et al., "Tau-lnduced Pathology in Epilepsy and Dementia: Notions from Patients and Animal Models" International Journal of Molecular Sciences 2018, 19:1092.
Simic et al., "Tau Protein Hyperphosphorylation and Aggregation in Alzheimer's Disease and Other Taupathies, and Possible Neuroprotective Strategies" Biomolecules (2016) 6:6.
Skillback et al., "Diagnostic Performance of Cerebrospinal Fluid Total Tau and Phosphorylated Tau in Creutzfeldt-Jakob Disease Results From the Swedish Mortality Registry" JAMA Neurol (2014) 71(4):476-483.
Spittaels et al., "Prominent Axonopathy in the Brain and Spinal Cord of Transgenic Mice Overexpressing Four-Repeat Human tau Protein" AJP (1999) 155(6):2153-2165.
Strong et al., "Alternations in Tau Metabolism in ALS and ALS-FTSD" Frontiers in Neurology (2020) 11:Article 598907.
Vuono et al., "The rule of tau in the pathological process and clinical expression of Huntington's disease" Brain (2015) 138:1907-1918.
Wallin et al., "Alzheimer's disease and cigarette smoke components: effects of nicotine, PAHs, and Cd(II), Cr(III, Pb(II), Pb (IV) ions on amyloid-β-peptide aggregation" Nature Scientific Reports (2017) 7:14423.
Zarranz et al., "Tau-Predominant-Associated Pathology in a Sporadic Late-Onset Hallervorden-Spatz Syndrome" Movement Disorders (2006) 21(1): 107-111.
Office Action dated Apr. 7, 2022 for Japanese Patent Application No. JP2020-512915 6, Filed May 11, 2018.

\* cited by examiner

COMPOUNDS FOR THE TREATMENT OF EPILEPSY, NEURODEGENERATIVE DISORDERS AND OTHER CNS DISORDERS

FIELD OF THE INVENTION

The present invention relates to novel compounds and to the novel compounds for use as a medicine for the prevention or treatment of epilepsy, neurodegenerative disorders and other CNS disorders. The present invention also relates to the use of said compounds for the manufacture of medicaments useful for treating epilepsy. The present invention further relates methods for the preparation of said novel compounds.

BACKGROUND OF THE INVENTION

Epilepsy is a neurological disorder in which affected patients are predisposed to generate epileptic seizures which can vary from uncontrolled jerking movement to as subtle as a momentary loss of awareness. Epilepsy has a prevalence of about 1% and is independent of socio-economic status, age or gender. The underlying causes of epilepsy (epileptogenesis) are heterogeneous and include both genetic and non-genetic risk factors (such as stroke or infection).

One mechanism underlying this disorder involves increased Voltage-gated calcium channels (VGCC) activity resulting in increased neurotransmitter release, $Ca^{2+}$ dyshomeostasis and neuronal hyperactivity, which may underlie at least in part epileptic seizures, TAU-phosphorylation and subsequent neuronal degeneration and neuronal death.

TAU is an intracellular protein with the ability to bind and consequently stabilize and define microtubule structure and function. Apart from this physiological function TAU also plays a direct role in disorders characterized by insoluble aggregates or polymers of tau which are formed by self-polymerization of tau monomers. The precise molecular mechanisms involved in TAU aggregation is not known but it appears to involve (partial) denaturation or misfolding of TAU in conformations with a high propensity to self-organize into higher order structures.

An important aspect of the TAU aggregation is its inherent cytotoxicity which reduces cellular integrity or even triggers cell death. One important aspect of toxic TAU aggregation in disease is hyper-phosphorylation of certain amino acid residues of the TAU protein. The hyper-phosphorylation of TAU appears to facilitate the cytotoxic aggregation process. Some of the kinases involved directly or indirectly in hyper-phosphorylation of TAU are mitogen-activated kinases ERK1 and/or ERK2. Intracellular $Ca^{2+}$ is an important trigger for activation of ERK1 and/or ERK2 activity and in this way $Ca^{2+}$ may enhance toxic TAU aggregation.

Although at present a host of therapeutic options exist still for epilepsy about 30% of the patient population is resistant to treatment, illustrating a large medical need. Moreover, current AEDs (anti-epileptic drugs) have side effects such as impaired cognitive performance which has a large negative impact on the quality of life of treated patients. Finally, current treatments are merely symptomatic and do not delay or stop epileptogenesis or neuronal degeneration after a primary insult.

Thus there is a need in the art for designing improved, more potent drugs for therapeutic treatments that target the underlying molecular mechanism epilepsy in particular treatments that lower neuronal hyperactivity with neuroprotective properties and/or without impairing cognitive performance.

SUMMARY OF THE INVENTION

A first aspect of the present invention provides a compound of formula (I) or a tautomer thereof,

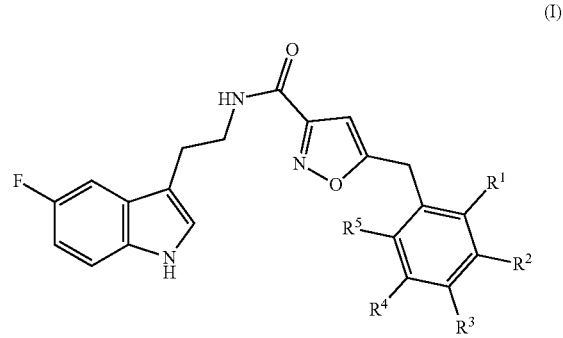

(I)

wherein, $R^1$ is selected from the group consisting of hydrogen; F, Cl, and Br;

$R^2$ is selected from the group consisting of hydrogen, F, Cl, and Br;

$R^3$ is selected from the group consisting of hydrogen, F, Cl, and Br;

$R^4$ is selected from the group consisting of hydrogen, F, Cl, and Br;

$R^5$ is selected from the group consisting of hydrogen, F, Cl, and Br;

with the proviso that at least one of $R^1$, $R^2$, $R^3$, $R^4$ or $R^5$ is not hydrogen;

with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt, or a prodrug thereof.

According to a second aspect, the present invention also encompasses a pharmaceutical composition comprising one or more pharmaceutically excipients and a therapeutically effective amount of a compound according to the first aspect of the invention or a salt thereof.

According to a third aspect, the present invention also encompasses a compound according to the first aspect of the invention, or a solvate, a hydrate, a salt, or a prodrug thereof, or a pharmaceutical composition according to the second aspect of the invention, for use as a medicament.

According to a fourth aspect, the present invention also encompasses a compound according to the first aspect of the invention, or a solvate, a hydrate, a salt, or a prodrug thereof, or a pharmaceutical composition according to the second aspect of the invention, for use as a medicine for the prevention and/or treatment of epilepsy, neurodegenerative disorders, pain disorders, anxiety disorders, depression, bipolar disorder, psychosis, drug withdrawal, tobacco withdrawal, memory loss, dementia, schizophrenia, panic.

According to a fifth aspect, the present invention also encompasses a compound according to the first aspect of the invention, or a solvate, a hydrate, a salt, or a prodrug thereof, or a pharmaceutical composition according to the second aspect of the invention, for use as a medicine for the prevention and/or treatment of epilepsy, Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The independent and dependent claims set out particular and preferred features of the invention. Features from the dependent claims may be combined with features of the independent or other dependent claims as appropriate.

BRIEF DESCRIPTION OF THE FIGURES

The following description of the figures of specific embodiments of the invention is merely exemplary in nature and is not intended to limit the present teachings, their application or uses.

(A) AT8 p-TAU, indicates the antibody recognising p-TAU phosphorylated on serine 202 and threonine 205
(B) AD2 p-TAU, indicates the antibody recognising p-TAU phosphorylated on serines 396 and 404
(C) phosphorylated TAU on T231
(D) phosphorylated TAU on S262.

Figure 7:
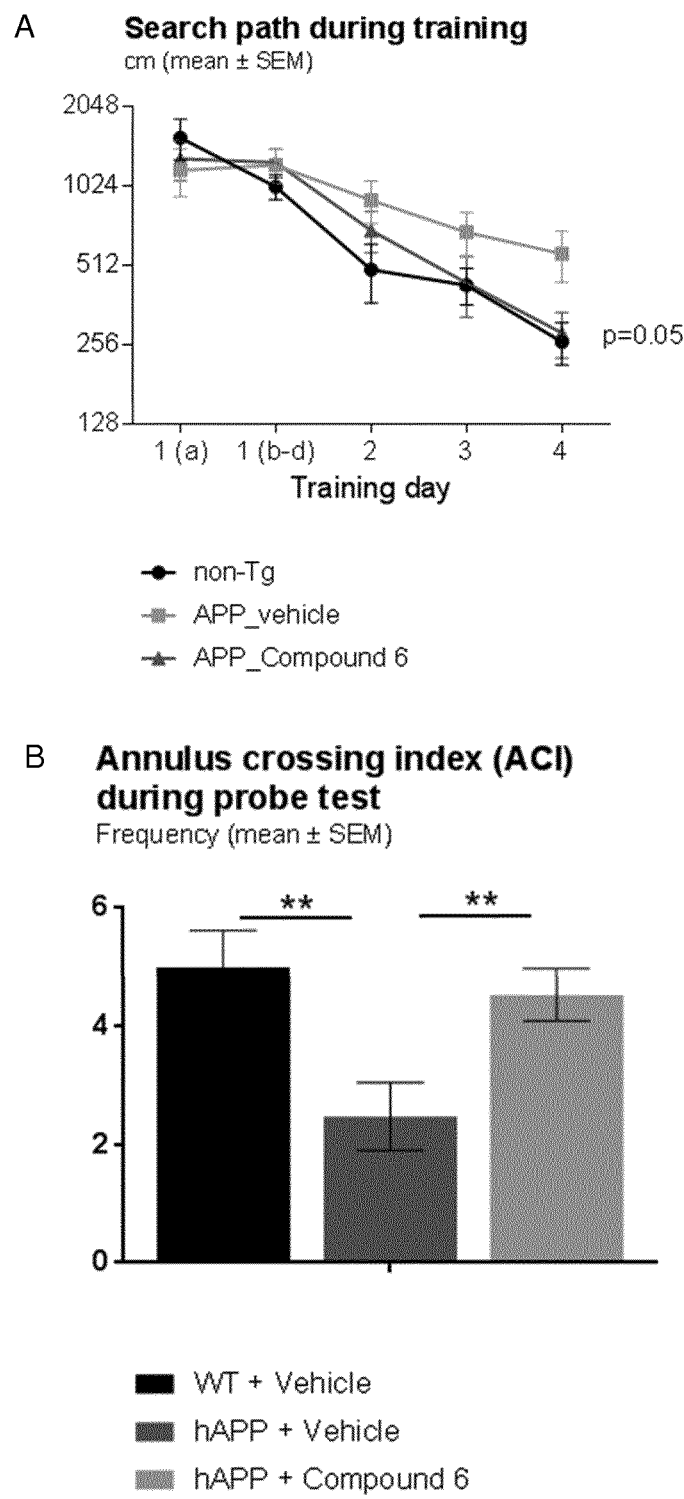

FIG. 7 shows the outcome of a Morris Water Maze test of transgenic APP mice treated with exemplary Compound 6. (A) shows the search path length during the training phase. P-value refers to the treatment of transgenic APP mice with exemplary Compound 6 versus vehicle. Section B shows the annulus crossing index (relative frequency of crossing an imaginary platform region) from the probe test. ** indicate $p<0.01$.

Figure 8:
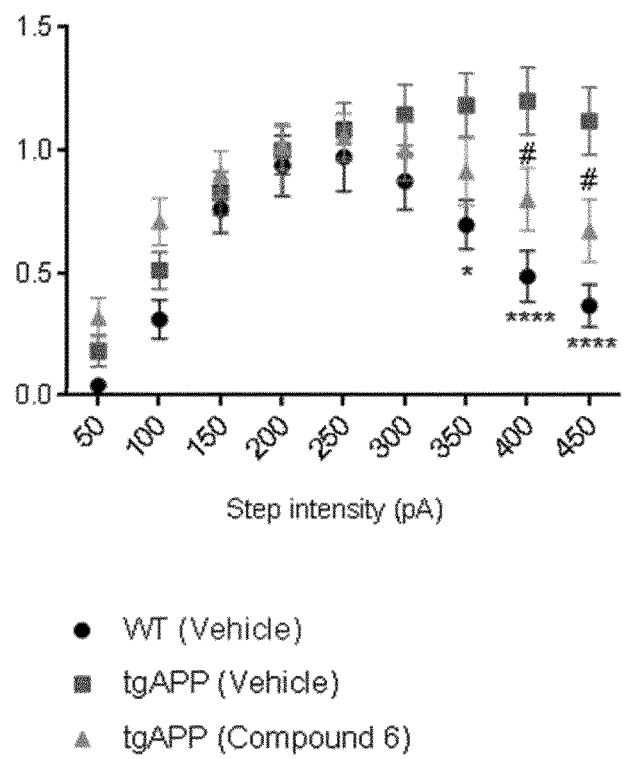

FIG. 8 represents a graph plotting neuronal firing rate of wild-type and tgAPP mice as a function of electrical stimulation (step intensity (pA)) for exemplary Compound 6. * and **** indicate $p<0.05$ and $p<0.0001$, respectively of wild type versus transgenic APP mice. # indicate $p<0.05$ of transgenic APP mice treated with vehicle versus Compound 6.

Figure 9:
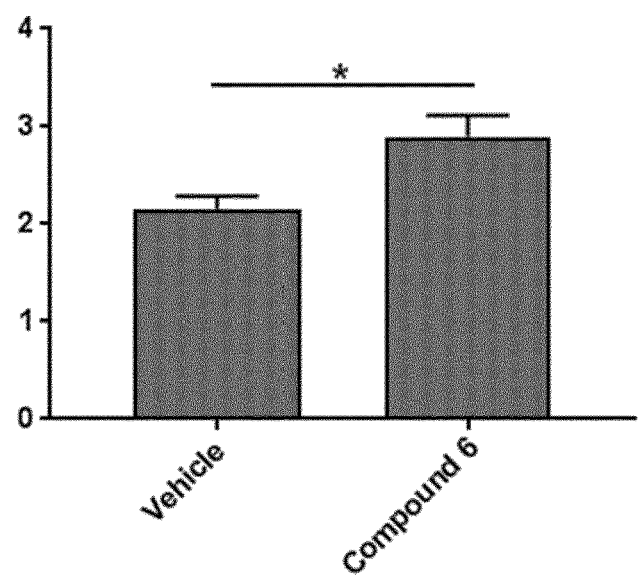

FIG. 9 represents a graph plotting the afterhyperpolarization (AHP) amplitude of single action potentials by somatic current clamp recordings using mouse brain slices incubated with vehicle or Compound 6. * indicates $p<0.05$.

DETAILED DESCRIPTION OF THE INVENTION

Before the present invention is described, it is to be understood that this invention is not limited to particular processes, methods, and compounds described, as such processes, methods, and compounds may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

The terms described above and others used in the specification are well understood to those in the art.

Whenever used in the present invention the term "compounds of the invention" or a similar term is meant to include the compounds of general formula (I) and any subgroup thereof. This term also refers to the compounds as depicted in Table 1 and their derivatives, N-oxides, salts, solvates, hydrates, tautomeric forms, analogues, pro-drugs, esters and metabolites, as well as their quaternized nitrogen analogues. The N-oxide forms of said compounds are meant to comprise compounds wherein one or several nitrogen atoms are oxidized to the so-called N-oxide.

Preferred statements (features) and embodiments of the compounds and processes of this invention are now set forth. Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Hereto, the present invention is in particular captured by any one or any combination of one or more of the below numbered statements 1-25 and embodiments with any other aspects and/or embodiment.

1. A compound of formula (I) or a tautomer thereof,

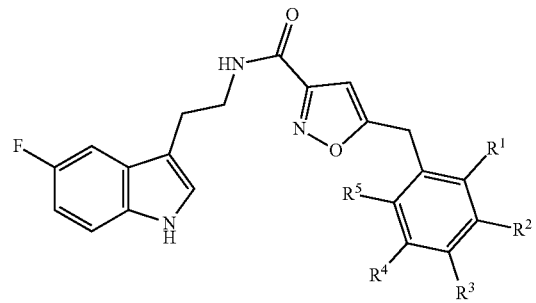

(I)

wherein, $R^1$ is selected from the group consisting of hydrogen; F, Cl, and Br;

$R^2$ is selected from the group consisting of hydrogen, F, Cl, and Br;

$R^3$ is selected from the group consisting of hydrogen, F, Cl, and Br;

$R^4$ is selected from the group consisting of hydrogen, F, Cl, and Br;

$R^5$ is selected from the group consisting of hydrogen, F, Cl, and Br;

with the proviso that at least one of $R^1$, $R^2$, $R^3$, $R^4$ or $R^5$ is not hydrogen;

with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt, or a prodrug thereof.

2. The compound according to statement 1, having any one of formula (II), (III), (IV), (V) or (VI)

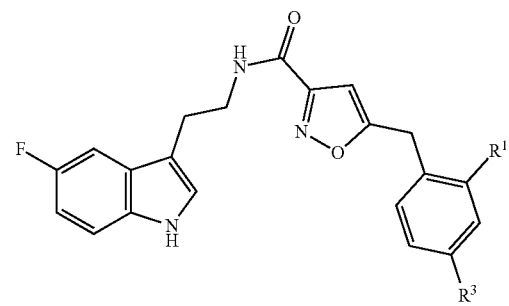

(II)

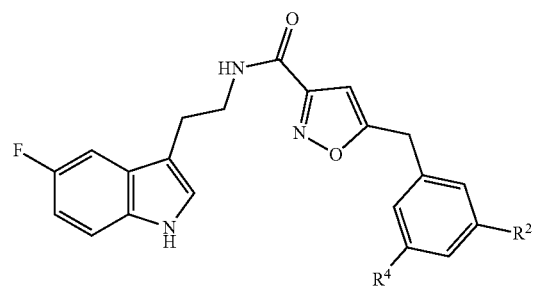

(III)

-continued (IV)

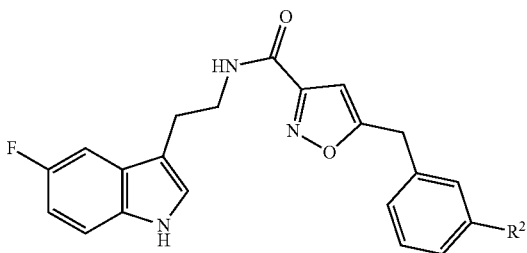

(V)

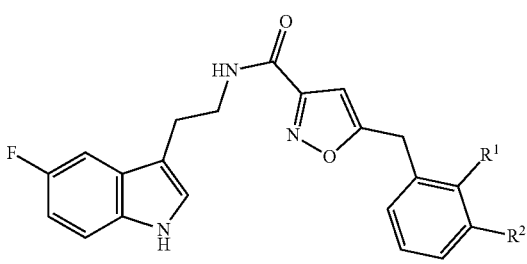

(VI)

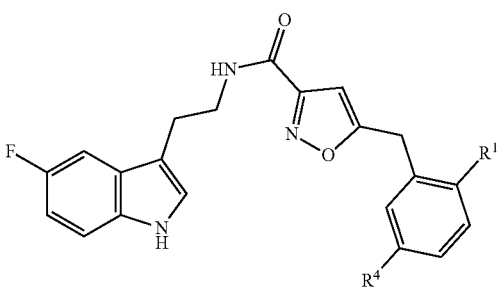

wherein $R^1$, $R^2$, $R^3$ and $R^4$ have the same meaning as defined in claim 1.

3. The compound according to statements 1 or 2, wherein $R^2$, $R^3$, $R^4$ and $R^5$ are hydrogen and wherein $R^1$ is selected from the group consisting of F, Cl, and Br, preferably, $R^1$ is F or Cl, preferably $R^1$ is F.

4. The compound according to statements 1 or 2, wherein $R^1$, $R^2$, $R^4$ and $R^5$ are hydrogen and $R^3$ is selected from the group consisting of F, Cl, and Br, preferably, $R^3$ is F or Cl, preferably $R^3$ is F.

5. The compound according to statements 1 or 2, wherein $R^2$, $R^4$ and $R^5$ are hydrogen and $R^1$ and $R^3$ are each independently selected from the group consisting of hydrogen; F, Cl, and Br; preferably $R^1$ and $R^3$ are each independently selected from the group consisting of hydrogen; and F.

6. The compound according to statements 1 or 2, wherein $R^3$, $R^4$ and $R^5$ are hydrogen and $R^1$ and $R^2$ are each independently selected from hydrogen; F, Cl, and Br; preferably $R^1$ and $R^2$ are each independently selected from the group consisting of hydrogen; and F.

7. The compound according to statements 1 or 2, wherein $R^2$, $R^3$ and $R^5$ are hydrogen and $R^1$ and $R^4$ are each independently selected from hydrogen; F, Cl, and Br; preferably $R^1$ and $R^4$ are each independently selected from the group consisting of hydrogen and F.

8. The compound according to statements 1 or 2, wherein $R^2$, $R^3$ and $R^5$ are hydrogen and $R^1$ and $R^5$ are each independently selected from hydrogen; F, Cl, and Br; preferably $R^1$ and $R^5$ are each independently selected from the group consisting of hydrogen and F.

9. The compound according to statements 1 or 2, wherein $R^1$, $R^4$ and $R^5$ are hydrogen and $R^2$ and $R^3$ are independently selected from hydrogen; F, Cl, or Br; preferably $R^2$ and $R^3$ are each independently selected from the group consisting of hydrogen and F.

10. The compound according to statements 1 or 2, wherein $R^1$, $R^3$ and $R^5$ are hydrogen and $R^2$ and $R^4$ are independently selected from hydrogen; F, Cl, Br; preferably $R^2$ and $R^4$ are each independently selected from the group consisting of hydrogen and F.

11. The compound according to statements 1 or 2, wherein $R^1$, $R^3$ and $R^4$ are hydrogen and $R^2$ and $R^5$ are independently selected from hydrogen; F, Cl, Br; preferably $R^2$ and $R^5$ are each independently selected from the group consisting of hydrogen and F.

12. The compound according to statements 1 or 2, wherein $R^1$, $R^2$, $R^3$, $R^4$ and $R^5$ are independently selected from hydrogen and F.

13. The compound according to statement 1, selected from the group consisting of:
  5-[(2,4-difluorophenyl)methyl]-N-[2-(5-fluoro-1H-indol-3-yl)ethyl]isoxazole-3-carboxamide;
  N-[2-(5-fluoro-1H-indol-3-yl)ethyl]-5-[(4-fluorophenyl)methyl]isoxazole-3-carboxamide;
  5-[(2,3-difluorophenyl)methyl]-N-[2-(5-fluoro-1H-indol-3-yl)ethyl]isoxazole-3-carboxamide;
  5-[(2,5-difluorophenyl)methyl]-N-[2-(5-fluoro-1H-indol-3-yl)ethyl]isoxazole-3-carboxamide;
  N-[2-(5-fluoro-1H-indol-3-yl)ethyl]-5-[(2-fluorophenyl)methyl]isoxazole-3-carboxamide;
  5-[(3,4-difluorophenyl)methyl]-N-[2-(5-fluoro-1H-indol-3-yl)ethyl]isoxazole-3-carboxamide; and
  5-[(3,5-difluorophenyl)methyl]-N-[2-(5-fluoro-1H-indol-3-yl)ethyl]isoxazole-3-carboxamide.

14. A pharmaceutical composition comprising one or more pharmaceutically excipients and a therapeutically effective amount of a compound according to any one of statements 1 to 13 and a solvate, a hydrate, a salt, or a prodrug thereof.

15. A compound according to any one of statements 1 to 13 or a pharmaceutical composition according to statement 14 for use as a medicament.

16. A compound according to any one of statements 1 to 13 or a pharmaceutical composition according to statement 14 for use as a medicine for the prevention and/or treatment of epilepsy, neurodegenerative disorders, pain disorders, anxiety disorders, depression, bipolar disorder, psychosis, drug withdrawal, tobacco withdrawal, memory loss, dementia, schizophrenia, and panic.

17. The compound according to statement 16, wherein the epilepsy is selected from the group consisting of refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seizures, absence seizures and atonic seizures, frontal lobe epilepsy, epilepsy with grand-mal seizures, generalized epilepsy, idiopathic epilepsy, symptomatic epilepsy, and cryptogenic epilepsy.

18. The compound according to statement 16, wherein the neurodegenerative disorder is selected from the group consisting of Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease.

19. The compound according to statement 16, wherein the pain disorder is selected from the group consisting of acute pain, persistent pain, chronic pain, inflammatory pain, and neuropathic pain.

20. The compound according to statement 16, wherein the anxiety disorder is selected from the group consisting of panic attack, agoraphobia or specific phobias, obsessive-compulsive disorders, post-traumatic stress disorder, acute stress disorder, generalized anxiety disorder, eating disorder, substance-induced anxiety disorder, and non-specified anxiety disorder.

21. A method of prevention and/or treatment of epilepsy, neurodegenerative disorders, pain disorders, anxiety disorders, depression, bipolar disorder, psychosis, drug withdrawal, tobacco withdrawal, memory loss, dementia, schizophrenia, panic, comprising administering an effective amount of a compound according to any one of statements 1 to 13, or a pharmaceutical composition according to statement 14 to a subject in need thereof.

22. The method according to statement 21, wherein the epilepsy is selected from the group consisting of refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seizures, absence seizures and atonic seizures.

23. The method according to statement 21, wherein the neurodegenerative disorder is selected from the group consisting of Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, and Creutzfeld-Jacob's disease.

24. The method according to statement 21, wherein the pain disorder is selected from the group consisting of acute pain, persistent pain, chronic pain, inflammatory pain and neuropathic pain.

25. The method according to statement 21, wherein the anxiety disorder is selected from the group consisting of panic attack, agoraphobia or specific phobias, obsessive-compulsive disorders, post-traumatic stress disorder, acute stress disorder, generalized anxiety disorder, eating disorder, substance-induced anxiety disorder, and non-specified anxiety disorder.

The compounds of the invention may be in the form of salts, preferably pharmaceutically acceptable salts, as generally described below. Some preferred, but non-limiting examples of suitable pharmaceutically acceptable organic and/or inorganic acids are as hydrochloric acid, hydrobromic acid, sulfuric acid, nitric acid, acetic acid and citric acid, as well as other pharmaceutically acceptable acids known per se (for which reference is made to the prior art referred to below).

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of the compounds of formula (I) and any subgroup thereof include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Pharmaceutically acceptable salts of compounds of formula (I) may be prepared by one or more of these methods:

(i) by reacting the compound of formula (I) with the desired acid;

(ii) by reacting the compound of formula (I) with the desired base;

(iii) by removing an acid- or base-labile protecting group from a suitable precursor of the compound of formula (I) or by ring-opening a suitable cyclic precursor, for example, a lactone or lactam, using the desired acid; or (iv) by converting one salt of the compound of formula (I) to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Britain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$CH$_3$)$_3$) polar head group. For more information, see Crystals and the Polarizing Microscope by N. H. Hartshorne and A. Stuart, 4$^{th}$ Edition (Edward Arnold, 1970), incorporated herein by reference.

All references to compounds of formula (I) or any subgroups thereof include references to salts, solvates, multi-component complexes and liquid crystals thereof and to solvates, multi-component complexes and liquid crystals of salts thereof.

The compounds of the invention include compounds of formula (I) or any subgroups thereof as hereinbefore defined, including all polymorphs and crystal habits thereof, prodrugs and isomers thereof (including optical, geometric and tautomeric isomers) as hereinafter defined and isotopically-labeled compounds of formula (I).

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention.

The invention also generally covers all pharmaceutically acceptable prodrugs or "pre-drugs" of the compounds of formula (I) or any subgroups thereof for which general reference is made to the prior art cited hereinbelow.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. The term "pre-drug", as used herein, means any compound that will be modified to form a drug species, wherein the modification may take place either inside or outside of the body, and either before or after the pre-drug reaches the area of the body where administration of the drug is indicated.

Included within the scope of the present invention are all geometric isomers and tautomeric forms of the compounds of formula (I) or any subgroups thereof, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC).

The compounds of formula (I) or any subgroups thereof may be prepared as described in the experimental section below using methods and chemistries with which those skilled in the art shall be familiar.

The present invention also encompasses pharmaceutical composition comprising at least one compound of the present invention. The present invention also encompasses pharmaceutical composition comprising at least one compound of the invention and at least one carrier, excipient or diluent acceptable for pharmaceutical purposes.

In some embodiments, the present invention relates to the use of at least one compound of formula (I), or any subgroups thereof, in (the preparation of a composition for) the prevention and/or treatment of epilepsy, neurodegenerative disorders, pain disorders, anxiety disorders, depression, bipolar disorder, psychosis, drug withdrawal, tobacco withdrawal, memory loss, dementia, schizophrenia, and panic.

In some embodiments, the present invention relates to a method of prevention and/or of treatment of epilepsy, neurodegenerative disorders, pain disorders, anxiety disorders, depression, bipolar disorder, psychosis, drug withdrawal, tobacco withdrawal, memory loss, dementia, schizophrenia, panic, comprising administering to a subject in need thereof an effective amount of at least one compound of formula (I), or any subgroups thereof, or a pharmaceutical composition comprising said at least one compound of formula (I) or any subgroups thereof.

In some embodiments, the present invention relates to the use of at least one compound of formula (I), or any subgroups thereof, in (the preparation of a composition for) the prevention and/or treatment of epilepsy, neurodegenerative disorders, pain disorders, anxiety disorders, depression, bipolar disorder, psychosis, drug withdrawal, tobacco withdrawal, memory loss, dementia, schizophrenia, panic; more preferably epilepsy and neurodegenerative disorders comprising Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, Creutzfeld-Jacob's disease; yet more preferably for the prevention and/or treatment of epilepsy and/or Alzheimer's disease.

In some embodiments, the present invention relates to the use of at least one compound of formula (I), or any subgroups thereof, in (the preparation of a composition for) the prevention and/or treatment of epilepsy, preferably wherein the epilepsy is selected from the group consisting of refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seizures, absence seizures and atonic seizures, frontal lobe epilepsy, epilepsy with grand-mal seizures, generalized epilepsy, idiopathic epilepsy, symptomatic epilepsy, and cryptogenic epilepsy.

In some embodiments, the present invention relates to the use of at least one compound of formula (I), or any subgroups thereof, in (the preparation of a composition for) the prevention and/or treatment of pain disorders, preferably wherein the pain disorder is selected from the group consisting of acute pain, persistent pain, chronic pain, inflammatory pain and neuropathic pain.

In some embodiments, the present invention relates to the use of at least one compound of formula (I), or any subgroups thereof, in (the preparation of a composition for) the prevention and/or treatment of anxiety disorders, preferably wherein the anxiety disorder is selected from the group consisting of panic attack, agoraphobia or specific phobias, obsessive-compulsive disorders, post-traumatic stress disorder, acute stress disorder, generalized anxiety disorder, eating disorder, substance-induced anxiety disorder, and non-specified anxiety disorder.

The term "subject" as used herein refers to a mammal. The subject will preferably be a human, but may also be a domestic livestock, laboratory or pet animals.

In some embodiments, at least one compound of formula (I) is used (for the preparation of a medicament) for preventing and/or treating a disease selected from the group consisting of epilepsy, neurodegenerative disorders, pain disorders, anxiety disorders, depression, bipolar disorder, psychosis, drug withdrawal, tobacco withdrawal, memory loss, dementia, schizophrenia, and panic and/or for preventing, treating and/or alleviating complications and/or symptoms associated therewith.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as tautomers, salts, hydrates or solvates thereof, may be administered as the raw chemical. Additionally, the active ingredient may be presented as a pharmaceutical composition.

Accordingly, the invention further provides pharmaceutical compositions that include effective amounts of compounds of formula (I), or tautomers, salts, hydrates, solvates, or prodrugs thereof, and one or more pharmaceutically acceptable carriers, diluents, or excipients. The compounds of formula (I) or tautomers, salts, hydrates or solvates thereof, are as herein described.

The compounds according to the invention may be administered as the sole active ingredient or together, i.e. in a fixed or free combination, with other therapeutic agents used in clinical practice for the treatment of those diseases listed above.

The compounds according to the invention and the other pharmaceutical active agent(s) may be administered together or separately and, when administered separately, administration may occur simultaneously or sequentially, in any order. The amounts of the compounds according to the invention and the other pharmaceutically active agent (s) and the relative timings of administration will be selected in order to achieve the desired combined therapeutic effect. The administration in combination of a compound of formula (I) or a tautomer, salt, hydrate or solvate thereof, with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

Appropriate cyclodextrins are α-, β- or γ-cyclodextrins (CDs) or ethers and mixed ethers thereof wherein one or more of the hydroxyl groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkoxycarbonylalkyl or carboxyalkoxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxyl groups are etherified with different groups such as, for example, hydroxypropyl and hydroxyethyl. An interesting way of formulating the compounds in combination with a cyclodextrin or a derivative thereof has been described in EP-A-721,331. Although the formulations described therein are with antifungal active ingredients, they are equally interesting for formulating the compounds. Said formulations may also be rendered more palatable by adding pharmaceutically acceptable sweeteners and/or flavors. In particular, the present invention encompasses a pharmaceutical composition comprising an effective amount of a compound according to the invention with a pharmaceutically acceptable cyclodextrin. The present invention also encompasses cyclodextrin complexes consisting of a compound according to the invention and a cyclodextrin.

Particular reference is made to the compositions, formulations (and carriers, excipients, diluents, etc. for use therein), routes of administration etc., which are known per se such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products, and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded, or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides, and derivatives thereof.

The preparations may be prepared in a manner known per se, which usually involves mixing the at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the formula (I) above that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a (pharmaceutical) composition for veterinary use that contains at least one compound of the invention and at least one suitable carrier (i.e. a carrier suitable for veterinary use). The invention also relates to the use of a compound of the invention in the preparation of such a composition.

EXAMPLES

The following examples are provided for the purpose of illustrating the present invention and by no means should be interpreted to limit the scope of the present invention.

Part A represents the preparation of the compounds (intermediates and final compounds) whereas Part B represents the pharmacological examples.

Part A

The compounds were prepared following two different synthetic pathways, illustrated in Scheme 1 and Scheme 2, shown below.

Scheme 1

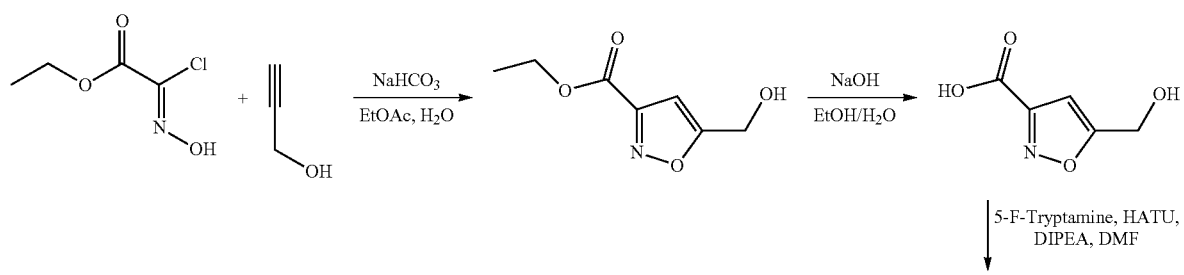

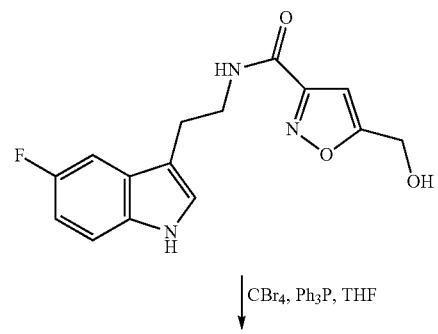

-continued

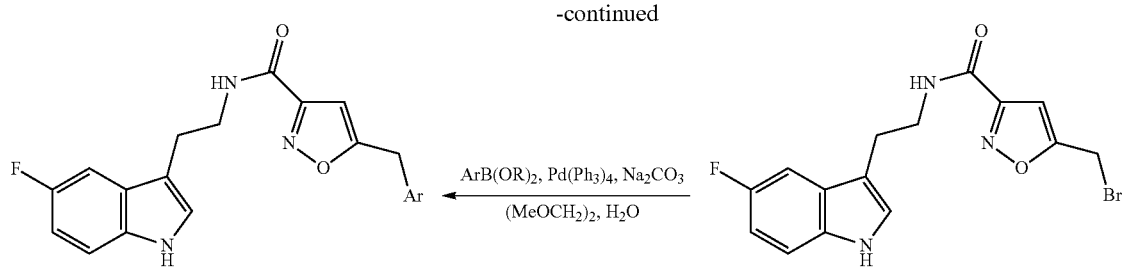

Scheme 2.

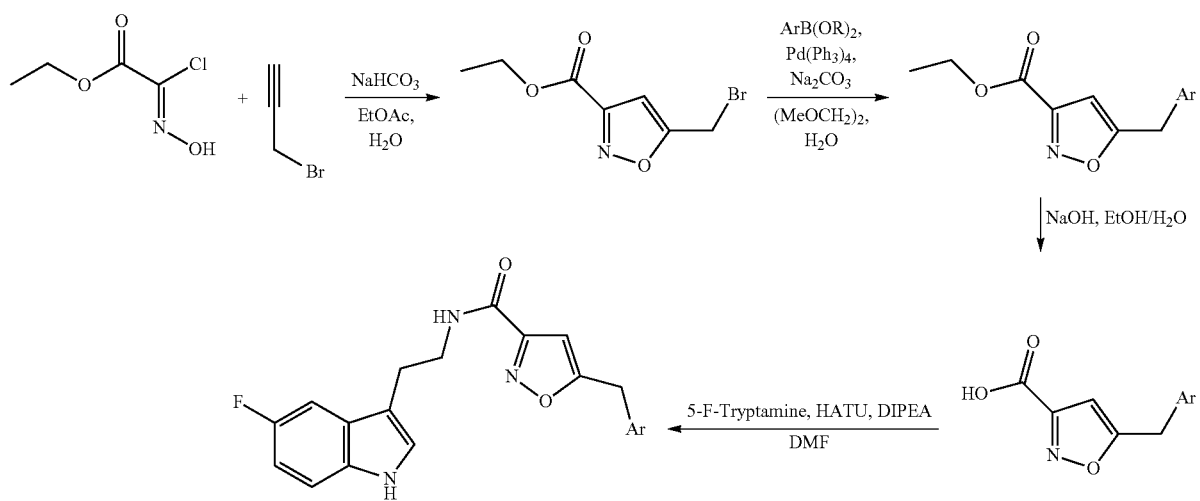

Intermediate I—Preparation of Ethyl 5-(bromomethyl)isoxazole-3-carboxylate

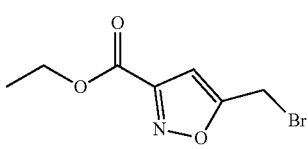

A solution of ethyl 2-chloro-2-(hydroxyimino)acetate (37.6 g, 240.66 mmol) in 200 mL of ethyl acetate was added dropwise at room temperature to a mixture of 3-bromoprop-1-yne (91 mL; 845 mmol), sodium bicarbonate (71.48 g; 842 mmol), ethyl acetate (1200 mL), and water (12 mL) and the mixture was stirred at room temperature for 108 hours. The solid was filtered off and the filtrate was washed twice with water, dried over magnesium sulfate and concentrated under reduced pressure. The residue was purified by flash chromatography on silica gel using a gradient of ethyl acetate (5-40%) in heptane to give 46.1 g (82%) of ethyl 5-(bromomethyl)isoxazole-3-carboxylate as a white solid. $^1$H NMR (CHLOROFORM-d) δ: 6.74 (s, 1H), 4.50 (s, 2H), 4.45 (q, 2H), 1.42 (t, 3H).

Intermediate II—preparation of Ethyl 5-(2,5-difluorobenzyl)isoxazole-3-carboxylate

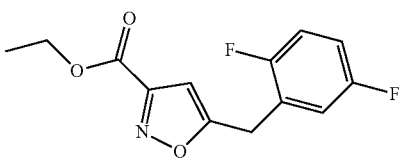 [SMILES: CCOC(=O)c1cc(Cc2cc(F)ccc2F)on1]

Twenty-five microwave vials were individually charged with ethyl 5-(bromomethyl)isoxazole-3-carboxylate (1.2 g; 5.13 mmol), 2,5-difluorophenylboronic acid (0.928 g; 5.64 mmol), tetrakis(triphenylphosphine)palladium(0) (0.297 g; 0.256 mmol), sodium carbonate (1.09 g; 10.25 mmol) and a mixture of water (2 mL) and 1,2-dimethoxyethane (8 mL) was added. The vials were sealed and heated at 130° C. in a microwave oven for 20 min. The content of the twenty-five vials was combined, diluted with ethyl acetate, and washed with water. The organic layer was concentrated under reduced pressure and the residue was purified by flash chromatography on silica gel using a gradient of ethyl acetate (5-40%) in heptane to give 18.47 g (54%) of ethyl 5-(2,5-difluorobenzyl)isoxazole-3-carboxylate as a yellow oil. $^1$H NMR (CHLOROFORM-d) δ: 6.90-7.12 (m, 3H), 6.42 (s, 1H), 4.42 (q, 2H), 4.15 (s, 2H), 1.40 (t, 3H). ESI/APCI(+): 268 (M+H), 290 (M+Na).

Intermediate III—Preparation of 5-(2,5-difluorobenzyl)isoxazole-3-carboxylic Acid

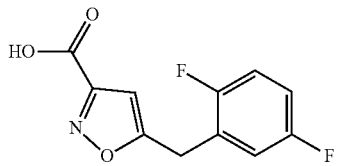 [SMILES: O=C(O)c1cc(Cc2cc(F)ccc2F)on1]

A solution of sodium hydroxide 1M (206 mL; 206 mmol) was added to a solution of ethyl 5-(2,5-difluorobenzyl) isoxazole-3-carboxylate (18.30 g; 68.48 mmol) in ethanol (20 mL). The mixture was stirred at room temperature for 2 hours. The solution was acidified to pH 1 by addition of a solution of hydrochloric acid 12N. The precipitate was collected by filtration and dried under reduced pressure to give 14.60 g (89%) of 5-(2,5-difluorobenzyl)isoxazole-3-carboxylic acid as a white solid. $^1$H NMR (DMSO-$d_6$) δ: 7.17-7.34 (m, 3H), 6.59 (s, 1H), 4.27 (s, 2H).

Intermediate IV—Preparation of Ethyl 5-(hydroxymethyl)isoxazole-3-carboxylate

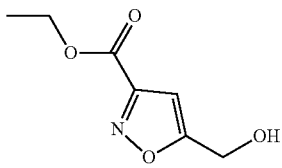

Propargyl alcohol (11.42 mL; 191.36 mmol) was added to a mixture of ethyl 2-chloro-2-(hydroxyimino)acetate (14.50 g; 95.68 mmol) and sodium hydrogen carbonate (16.08 g; 191.36 mmol) in ethyl acetate (400 mL) and water (40 mL) and stirred at room temperature for 24 hours. The two phases were separated and the organic layer was concentrated under reduced pressure. The crude mixture was purified by flash chromatography on silica (eluent 1 to 10% ethyl acetate in dichloromethane) to yield 8.67 g (53%) of ethyl 5-(hydroxymethyl)isoxazole-3-carboxylate as an oil.

Intermediate V—Preparation of 5-(hydroxymethyl)isoxazole-3-carboxylic Acid

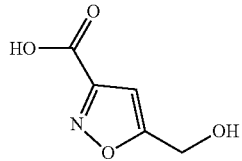

A solution of sodium hydroxide in water (2M; 50 mL) was added to a mixture of ethyl 5-(hydroxymethyl)isoxazole-3-carboxylate (8.67 g; 50.66 mmol) in ethanol (30 mL) and stirred vigorously for 2 hours. The solution was concentrated under reduced pressure, diluted in water and extracted with dichloromethane. The aqueous layer was acidified to pH 1 with hydrochloric acid 6N and extracted several times with ethyl acetate. The organic layer was dried and concentrated under reduced pressure to yield 5.43 g (75%) of 5-(hydroxymethyl)isoxazole-3-carboxylic acid as a white solid.

Intermediate VI—Preparation of N-(2-(5-fluoro-1H-indol-3-yl)ethyl)-5-(hydroxymethyl)isoxazole-3-carboxamide

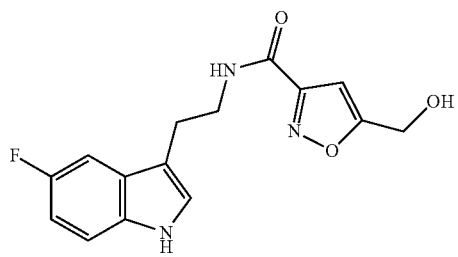 [SMILES: O=C(NCCc1c[nH]c2ccc(F)cc12)c1cc(CO)on1]

N,N diisopropylethylamine (10.75 mL; 58.23 mmol) was added to mixture of 2-(5-fluoro-1H-indol-3-yl)ethanamine hydrochloride (5.00 g; 23.29 mmol), O-(7-azabenzotriazol-1-yl)-N,N,N',N'-tetramethyluronium hexafluorophosphate (8.86 g; 23.29 mmol) and 5-(hydroxymethyl)isoxazole-3-carboxylic acid (3.67 g; 25.62 mmol) in dry DMF (40 mL) and stirred at room temperature overnight. The reaction mixture was concentrated under reduced pressure and diluted in ethyl acetate, washed subsequently with an aqueous solution of potassium hydrogensulfate (1M) and an aqueous solution of sodium carbonate (1M). The organic layer was dried with magnesium sulfate and concentrated under reduced pressure. The crude residue was purified by flash column chromatography on silica (eluent methanol 0 to 10% in dichloromethane) to yield 5.26 g (74%) of N-(2-(5-fluoro-1H-indol-3-yl)ethyl)-5-(hydroxymethyl)isoxazole-3-carboxamide as a sticky yellowish solid.

Intermediate VII—Preparation of 5-(bromomethyl)-N-(2-(5-fluoro-1H-indol-3-yl)ethyl)isoxazole-3-carboxamide

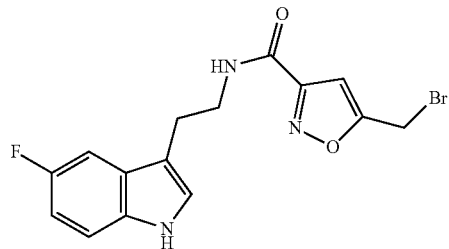 [SMILES: O=C(NCCc1c[nH]c2ccc(F)cc12)c1cc(CBr)on1]

A solution of N-(2-(5-fluoro-1H-indol-3-yl)ethyl)-5-(hydroxymethyl)isoxazole-3-carboxamide (5.30 g; 17.48 mmol) in THF (10 mL) was added to a solution of perbromomethane (8.69 g; 26.21 mmol) and triphenylphosphine (6.88 g; 26.21 mmol) in THF (60 mL). The resulting solution was stirred at room temperature for 2.5 hours. The solid was filtered off and the solution was concentrated under reduced pressure. The residue was purified by flash column chromatography on silica (eluent ethyl acetate 15 to 100% in heptane) to yield 2.64 g (41%) 5-(bromomethyl)-N-(2-(5- fluoro-1H-indol-3-yl)ethyl)isoxazole-3-carboxamide as a white solid. ESI/APCI(+): 366, 368 (M+H). ESI/APCI(−): 366, 364 (M−H).

Preparation of Compounds of the Invention

Example 1—Preparation of 5-(2,5-difluorobenzyl)-N-(2-(5-fluoro-1H-indol-3-yl)ethyl)isoxazole-3-carboxamide

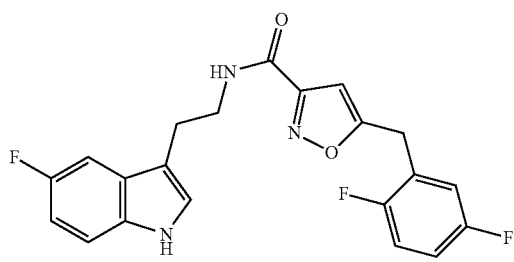 [SMILES: O=C(NCCc1c[nH]c2ccc(F)cc12)c1cc(Cc2cc(F)ccc2F)on1]

N-Ethyldiisopropylamine (25.65 mL; 148.37 mmol) was added to a stirred mixture of 2-(5-fluoro-1H-indol-3-yl)ethan-1-amine hydrochloride (13.00 g; 59.35 mmol), 5-(2,5-difluorobenzyl)isoxazole-3-carboxylic acid (14.19 g; 59.35 mmol), and O-(7-azabenzotriazol-1-yl)-N,N,N',N'-tetramethyluronium hexafluorophosphate (22.57 g; 59.35 mmol.) in dry DMF (90 mL). The mixture was stirred at room temperature for 60 hours and then was concentrated under reduced pressure. The residue was dissolved in ethyl acetate and the solution was washed with water and brine, dried over magnesium sulfate, filtered, and concentrated under reduced pressure. The residue was purified by flash chromatography on silica gel using a gradient of ethyl acetate (1-10%) in dichloromethane to give 20.02 g of a yellowish solid which was recrystallized in a mixture of dichloromethane and n-heptane to yield 19.06 g (80%) of 5-(2,5-difluorobenzyl)-N-(2-(5-fluoro-1H-indol-3-yl)ethyl)isoxazole-3-carboxamide as a white solid.

or 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2,5-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.038 g (23%) 5-(2,5-difluorobenzyl)-N-(2-(5-fluoro-1H-indol-3-yl)ethyl)isoxazole-3-carboxamide as a white solid.

$^1$H NMR (DMSO-$d_6$) δ: 10.92 (br. s., 1H), 8.82 (t, 1H), 7.1-7.38 (m, 6H), 6.90 (td, 1H), 6.53 (s, 1H), 4.26 (s, 2H), 3.48 (q, 2H), 2.88 (t, 2H). ESI/APCI(+): 400 (M+H). ESI/APCI(−): 398 (M−H).

Example 2—Preparation of 5-(2,4-difluorobenzyl)-N-(2-(5-fluoro-1H-indol-3-yl)ethyl)isoxazole-3-carboxamide

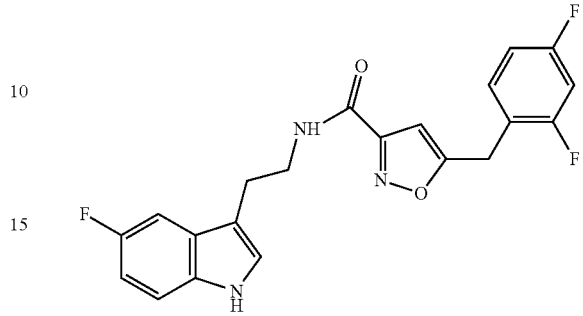

5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2,4-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.0462 g (28%) of 5-(2,4-difluorobenzyl)-N-(2-(5-fluoro-1H-indol-3-yl)ethyl) isoxazole-3-carboxamide as a white solid. $^1$H NMR (300 MHz, DMSO-$d_6$): δ 10.92 (br. s., 1H); 8.82 (t, 1H); 7.39-7.57 (m, 1H); 7.21-7.36 (m, 4H); 7.11 (td, 1H); 6.90 (td, 1H); 6.50 (s, 1H); 4.24 (s, 2H); 3.49 (q, 2H); 2.89 (t, 2H). ESI/APCI(+): 400 (M+H). ESI/APCI(−): 398 (M−H).

Example 3—Preparation of 5-(3,4-difluorobenzyl)-N-(2-(5-fluoro-1H-indol-3-yl)ethyl)isoxazole-3-carboxamide

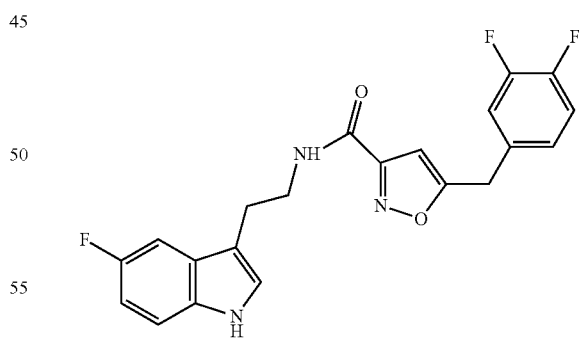

5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (3,4-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.065 g (40%) 5-(3,4-difluorobenzyl)-N-(2-(5-fluoro-1H-indol-3-yl)ethyl)isoxazole-3-carboxamide as a pale yellow solid. $^1$H NMR (300 MHz, DMSO-d$_6$) δ ppm 10.92 (br. s., 1H); 8.81 (t, 1H) 7.36-7.49 (m, 2H); 7.28-7.35 (m, 2H); 7.25 (d, 1H); 7.12-7.21 (m, 1H); 6.90 (td, 1H); 6.54 (s, 1H); 4.23 (s, 2H); 3.48 (q, 2H); 2.89 (t, 2H). ESI/APCI(+): 400 (M+H). ESI/APCI(−): 398 (M−H).

Example 4—Preparation of 5-(3,5-difluorobenzyl)-N-(2-(5-fluoro-1H-indol-3-yl)ethyl)isoxazole-3-carboxamide

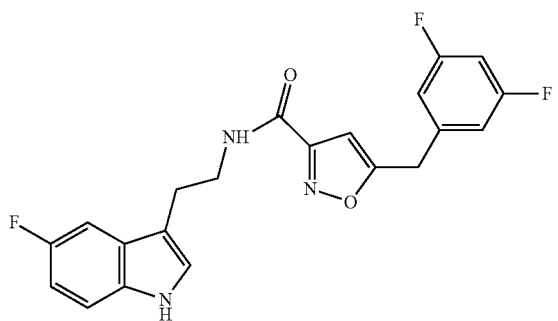 [SMILES: O=C(NCCc1c[nH]c2ccc(F)cc12)c1cc(Cc2cc(F)cc(F)c2)on1]

5-(bromomethyl)-N-(2-(5-fluoro-1H-indol-3-yl)ethyl)isoxazole-3-carboxamide (0.150 g; 0.409 mmol) was dissolved in DME (3 mL) and water (1 mL) with (3,5-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.068 g (41%) of 5-(3,5-difluorobenzyl)-N-(2-(5-fluoro-1H-indol-3-yl)ethyl)isoxazole-3-carboxamide as a white solid. $^1$H NMR (300 MHz, DMSO-d$_6$) δ ppm 10.93 (br. s, 1H.); 8.83 (t, 1H); 7.03-7.42 (m, 6H); 6.91 (td, 6H); 6.59 (s, 1H); 4.27 (s, 2H); 3.50 (q, 2H); 2.90 (t, 2H). ESI/APCI(+): 400 (M+H). ESI/APCI(−): 398 (M−H).

Example 5—Preparation of N-(2-(5-fluoro-1H-indol-3-yl)ethyl)-5-(4-fluorobenzyl)isoxazole-3-carboxamide

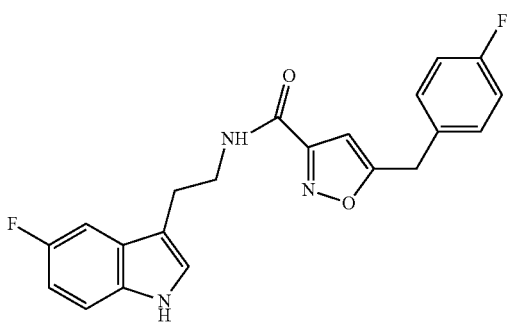 [SMILES: O=C(NCCc1c[nH]c2ccc(F)cc12)c1cc(Cc2ccc(F)cc2)on1]

5-(bromomethyl)-N-(2-(5-fluoro-1H-indol-3-yl)ethyl)isoxazole-3-carboxamide (0.150 g; 0.409 mmol) was dissolved in DME (3 mL) and water (1 mL) with (4-fluorophenyl)boronic acid (0.086 g; 0.430 mmol), N,N diisopropylethylamine (0.151 mL; 0.819 mmol), [1,1'-Bis(diphenylphosphino)ferrocene]dichloropalladium(II) (0.033 g; 0.040 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.088 g (57%) N-(2-(5-fluoro-1H-indol-3-yl)ethyl)-5-(4-fluorobenzyl)isoxazole-3-carboxamide as a white solid. $^1$H NMR (300 MHz, DMSO-d$_6$) δ ppm 10.92 (br. s., 1H,); 8.80 (t, 1H); 7.11-7.42 (m; 7H); 6.81-6.99 (m, 1H); 6.51 (s, 1H); 4.21 (s, 2H); 3.48 (q, 2H); 2.88 (t, 2H). ESI/APCI(+): 382 (M+H). ESI/APCI(−): 380 (M−H).

Example 6—Preparation of 5-(2,3-difluorobenzyl)-N-(2-(5-fluoro-1H-indol-3-yl)ethyl)isoxazole-3-carboxamide

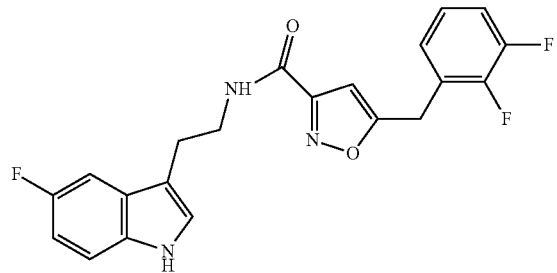 [SMILES: O=C(NCCc1c[nH]c2ccc(F)cc12)c1cc(Cc2cccc(F)c2F)on1]

5-(bromomethyl)-N-(2-(5-fluoro-1H-indol-3-yl)ethyl)isoxazole-3-carboxamide (0.200 g; 0.546 mmol) was dissolved in DME (3 mL) and water (1 mL) with (2,3-difluorophenyl)boronic acid (0.129 g; 0.819 mmol), N,N diisopropylethylamine (0.201 mL; 1.09 mmol), Bis(diphenylphosphino)ferrocene]dichloropalladium(II) (0.045 g; 0.056 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 20 to 100% in heptane) to yield 0.015 g (7%) 5-(2,3-difluorobenzyl)-N-(2-(5-fluoro-1H-indol-3-yl)ethyl)isoxazole-3-carboxamide as a white solid. $^1$H NMR (300 MHz, DMSO-d$_6$) δ ppm 10.85-11.04 (m, 1H); 8.82 (t, 1H); 7.45-7.30 (1H, m); 7.28-7.36 (m, 2H); 7.17-7.27 (m, 3H); 6.90 (td, 1H); 6.55 (s; 1H); 4.33 (s; 2H); 3.48 (d, 2H); 2.88 (t, 2H). ESI/APCI(+): 400 (M+H). ESI/APCI(−): 398 (M−H).

Example 7—Preparation of N-(2-(5-fluoro-1H-indol-3-yl)ethyl)-5-(2-fluorobenzyl)isoxazole-3-carboxamide

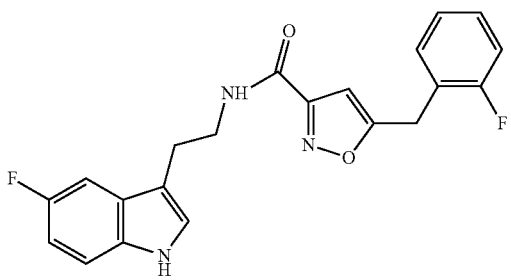 [SMILES: O=C(NCCc1c[nH]c2ccc(F)cc12)c1cc(Cc2ccccc2F)on1]

5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2-fluorophenyl)boronic acid (0.086 g; 0.430 mmol), N,N diisopropylethylamine (0.151 mL; 0.819 mmol), Bis(diphenylphosphino)ferrocene]dichloropalladium(II) (0.033 g; 0.040 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.068 g (44%) N-(2-(5-fluoro-1H-indol-3-yl)ethyl)-5-(2-fluorobenzyl)isoxazole-3-carboxamide as a white solid. $^1$H NMR (300 MHz, DMSO-d$_6$) δ ppm 10.93 (br. s., 1H); 8.66-8.96 (m, 1H); 7.13-7.52 (m, 7H); 6.79-7.00 (m, 1H); 6.51 (s, 1H); 4.26 (s, 2H); 3.49 (q, 2H); 2.89 (t, 2H). ESI/APCI(+): 382 (M+H).
ESI/APCI(−): 380 (M−H).
Part B

Example 8—Construction of a TAU Gene Over-Expressing Cell Line

A TAU expression plasmid was constructed by subcloning the cDNA of human TAU-P301L (encoding for TAU with proline 301 substituted by a leucine residue) into mammalian expression vector pcDNA3.1 resulting in plasmid pcDNA3.1-TAU P301L. Plasmids pcDNA3.1 and pcDNA3.1-TAU P301L were transfected to human neuroblastoma cells (BM17; ATCC No. CRL-2267) and independent clonal lines with the plasmids stably integrated into the genome were selected. These resulted in cell lines named M17-3.1 and M17-TAU(P301L) (transfected with pcDNA3.1 and pcDNA3.1-TAU P301L, respectively). Expression of the TAU P301L genes in the cell lines was confirmed by Western analysis.

Example 9—Use of P301L TAU Expressing Cells as a Model of Neuronal Degeneration The expression of TAU P301L in M17-TAU(P301L) cells was found to confer increased toxicity relative to control cells expressing wild type TAU (M17-TAUwt).

In degenerated or dead cells lactate dehydrogenase (LDH) leaks out of the cells into the extracellular environment due to a loss of plasma-membrane integrity. This principle was used to determine cytotoxicity by quantifying the level of leaked LDH into the growth medium relative to the sum of total LDH activity from living cells and dead cells.

The detailed method for determining cytotoxicity was as follows: From appropriate precultures of M17-3.1 and M17-TAU(P301L) cells were seeded at 2500 cells/cm2 in Optimem Reduced Serum without phenol red (Gibco, Cat. 31985-047) supplemented with 1% fetal calf serum, 1 mM sodium pyruvate, 1× non-essential amino acids, 500 μg/ml G418 0,5× antibiotic/antimycotic. After 3 hours of incubation at 37° C./5% CO2 1 volume of Optimem Reduced Serum (same as described above; except without fetal calf serum) supplemented with 2.5 μM all-trans retinoic acid (ATRA) was added. The cells were further incubated for 7 days. Subsequently, LDH activity was determined using Promega Cytotox 96 Non-Radioactive cytotoxicity assay, (Cat. G1780) according the supplier's instructions.

Figure 1:
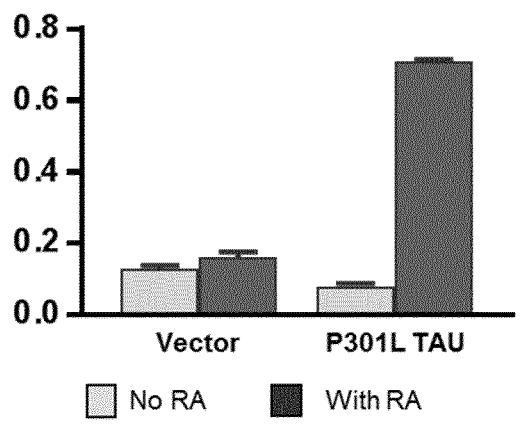
FIG. 1 Section A represents a graph plotting the percentage of LDH leaked into the medium by each of M17-TAU P301L cells (P301L TAU), and M17-3.1 cells (vector) in the presence and absence of all-trans retinoic acid (RA). Section B represents a graph plotting the relative levels of cytosolic calcium in the M17-TAU P301L cells in the presence and absence of retinoic acid (RA). **** indicate $p<0.0001$.
Figure 1:
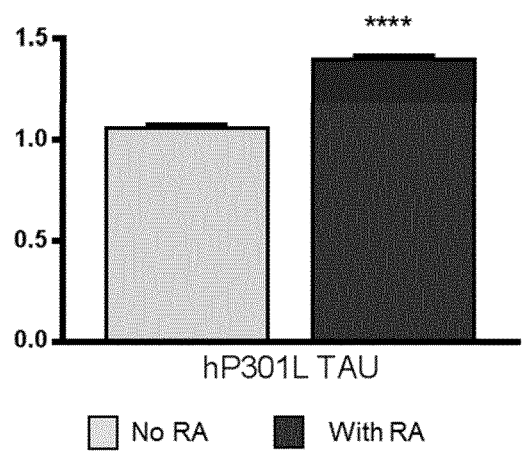

FIG. 1A shows that of M17-TAU P301L cells, but not of M17-3.1 cells display a relatively high level of LDH leaked into the medium demonstrating toxicity specifically provoked by TAU P301. Highlighting the sensitivity of a TAU(301) expressing neuroblastoma cell line to retinoic acid-instigated differentiation.

Example 10—Use of the P301L TAU Expressing Cells as a Model for of Calcium Dyshomeostasis Cystosic calcium was measured by loading the cells with a medium containing Fura-2 AM (Sigma-Aldrich), a cell permeable fluorescent probe for $Ca^{2+}$. Fura-2-AM was dissolved in DMSO plus 20% Pluronic Acid (F-127) (Invitrogen) in a 1:1 ratio and diluted in medium to a final concentration of 0.5 μM. To this loading medium probenecid (Sigma-Aldrich) was added to a final concentration of 2.5 mM. Then, culture medium was replaced by loading medium and after incubation for 1 hour at 37° C. cells were washed twice and replaced with HBSS (Gibco) supplemented with 0.2% FBS and 0.02M HEPES. Next, changes in cytosolic calcium were measured using a FlexStation 3 microplate reader (Molecular Devices) and quantified ratiometric, by calculating changes in the amount of cytosolic $Ca^{2+}$ bound Fura-2 (fluorescence intensity at 340 nm) relative to the amount of $Ca^{2+}$ unbound Fura-2 (fluorescence intensity at 380 nm). Data was processed in SoftMax Pro 5.4.6 software (Molecular Devices).

FIG. 1B shows that in P301L TAU expressing cells in which toxicity was induced by ATRA according the method of Example 9, displayed increased levels of cytosolic calcium.

Figure 2:
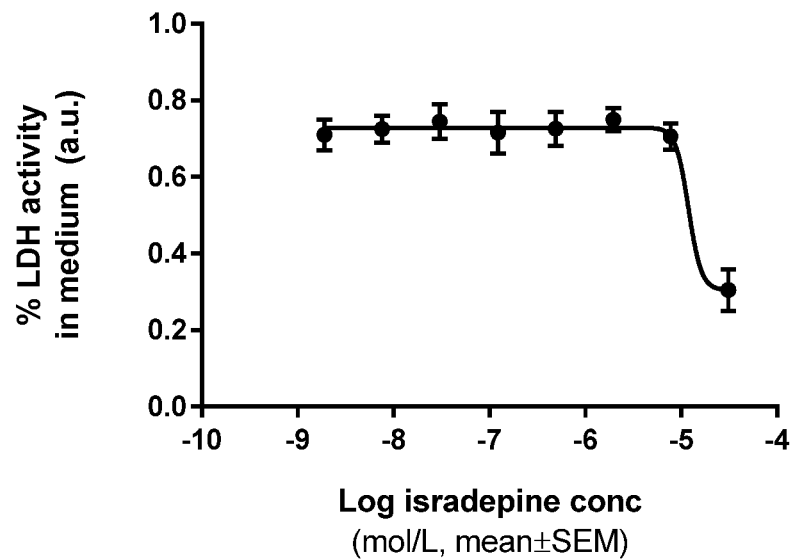
FIG. 2 represents a graph plotting the percentage of LDH activity leaked into the medium by M17-TAU P301L cells in the presence of RA as a function of the concentration of isradepine added to the cells.

Example 11—Use of the P301L TAU Expressing Cells as a Model for Neurodegeneration in the Screening Compounds for the Treatment of Epilepsy The cell line model of TAU-induced cytotoxicity allows identification of compounds which can be used in transgenic animals and human patients for the treatment of epilepsy. Isradepine is a voltage-gated calcium channel (VGCC) inhibitor a well-established target for treating epilepsy and iradepine is active in models of epilepsy. FIG. 2 shows toxicity is reduced of RA-incubated cells that were treated with voltage-gated calcium channel (VGCC) isradepine.

Example 12—Use of the TAU Expressing Cells in the Screening of Exemplary Compounds of this Invention The M17-TAU P301L cell line made it possible to assess the ability of novel compounds to counteract TAU cytotoxicity. Active inhibitors of TAU cytotoxicity were found to inhibit LDH leakage of M17-TAU P301L cells treated as described in Example 9. Efficacy (potency) of the compounds was determined by testing compounds at different concentrations ranging from non-effective (thus at a relatively low concentration) to an effective concentration for their ability to reduce LDH activity of retinoic acid incubated M17-TAU P301L cells. These measurements were used to calculate $EC_{50}$ values.

Exemplary compounds of the present invention are shown in Table 1, with their chemical structure and their $EC_{50}$ value (expressed in μg/ml) as determined from example 12 in the TAU-induced toxicity experiment.

TABLE 1

| Compound | Structure | $EC_{50}$ (μg/ml) |
|---|---|---|
| 1 | 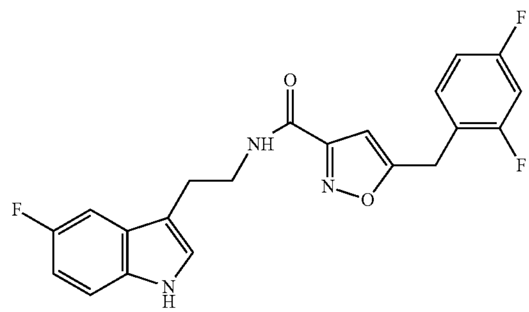 [SMILES: O=C(NCCc1c[nH]c2ccc(F)cc12)c1cc(Cc2ccc(F)cc2F)on1] | 0.0020 |
| 2 | 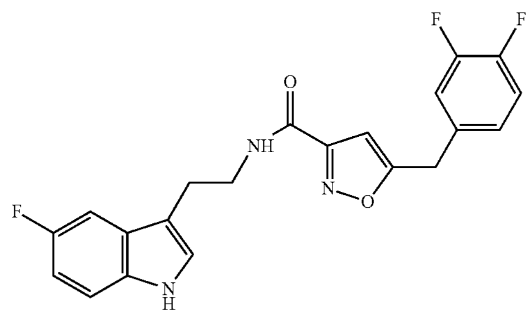 [SMILES: O=C(NCCc1c[nH]c2ccc(F)cc12)c1cc(Cc2ccc(F)c(F)c2)on1] | 0.0020 |
| 3 | 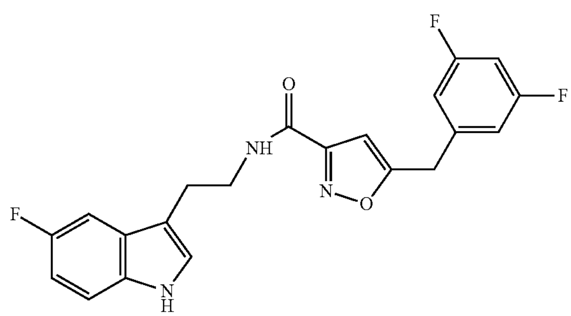 [SMILES: O=C(NCCc1c[nH]c2ccc(F)cc12)c1cc(Cc2cc(F)cc(F)c2)on1] | 0.0021 |
| 4 | 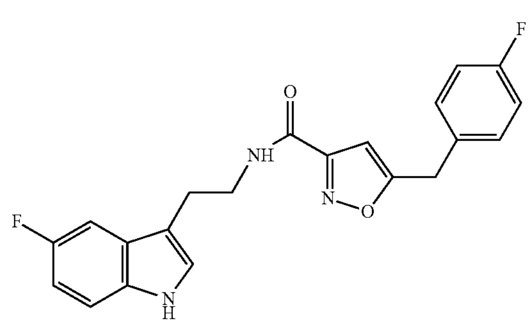 [SMILES: O=C(NCCc1c[nH]c2ccc(F)cc12)c1cc(Cc2ccc(F)cc2)on1] | 0.0022 |

TABLE 1-continued

| Compound | Structure | EC$_{50}$ (µg/ml) |
|---|---|---|
| 5 | 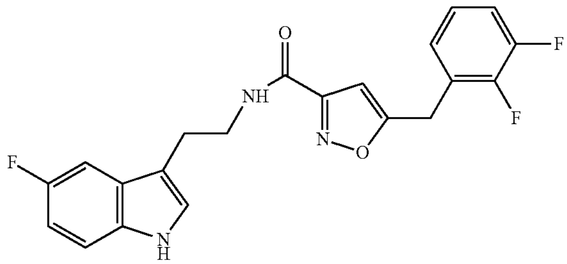 [SMILES: O=C(NCCc1c[nH]c2ccc(F)cc12)c1cc(Cc2cccc(F)c2F)on1] | 0.0028 |
| 6 | 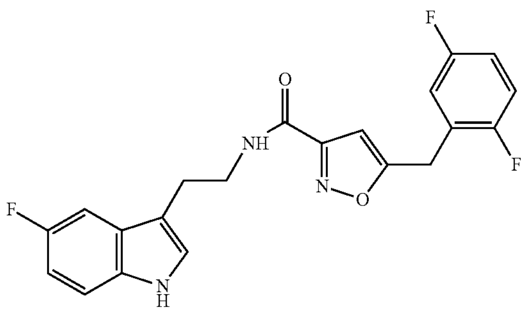 [SMILES: O=C(NCCc1c[nH]c2ccc(F)cc12)c1cc(Cc2cc(F)ccc2F)on1] | 0.0034 |
| 7 | 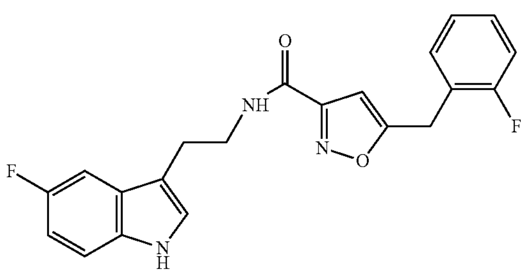 [SMILES: O=C(NCCc1c[nH]c2ccc(F)cc12)c1cc(Cc2ccccc2F)on1] | 0.0043 |

Figure 3:
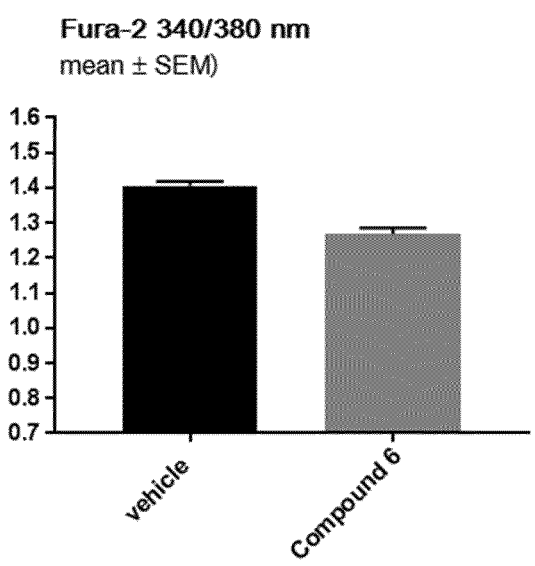
FIG. 3 represents a graph plotting the relative levels of cytosolic calcium in M17-TAU P301L cells, after being challenged with retinoic acid, in the presence of vehicle or exemplary Compound 6 at 625 nM. *** indicate $p<0.001$.

In addition compounds were tested to lower the elevated cytosolic calcium levels. In the presence of the compounds these cytosolic calcium levels were decreased. FIG. 3 shows that the compounds mitigate the calcium dyshomeostasis under conditions of toxicity in the M17-TAU P301L cell line model described in Example 9.

Example 13—Ex-Vivo Inhibition of Oligomeric Amyloid Beta Toxicity

Figure 4:
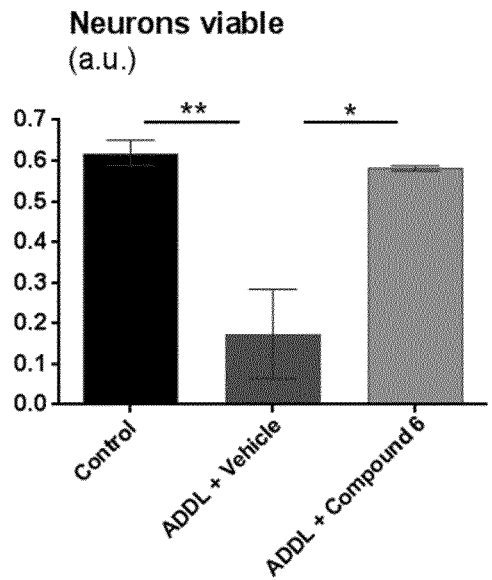
FIG. 4 represents a graph plotting relative number of viable primary neurons after being challenged with amyloid-derived diffusible ligands (ADDLs), in the presence of vehicle or exemplary Compound 6. * indicates $p<0.05$ and ** indicate $p<0.01$.

An exemplary compound of this invention was tested for its ability to inhibit toxicity elicited by oligomeric amyloid beta (Aβo). Neurons from rat embryos were harvested and cultured using standard methods (such as used in Schlager et al., 2014. Cell reports, 8(5), pp. 1248-56.). Differentiated neurons were challenged with Aβo and viability was quantified. Aβo treatment led to severely reduced neuronal viability, whereas viability was strongly rescued in Aβo treated neurons in the presence of 100 ng/mL Compound 6 (FIG. 4). These results demonstrate that Compound 6 strongly mitigates Aβo instigated neuronal cell death.

Detailed Methods:

At day in-vitro 19 days after isolation primary hippocampal neurons were transfected with Marcks-GFP in order to visualize the neurons with fluorescence microscopy.

Preparation of ADDL's to Generate Aβo:

ADDL (Abeta-derived diffusible ligands) preparation (representing Aβo) was done according to Klein (Klein, 2002. Neurochemistry international, 41(5), pp. 345-52.). Abeta 1-42 was purchased from AnaSpec Inc. and dissolved in HFIP to homogenize the peptide. HFIP was then evaporated in a speedvac and Abeta film was dried at −20° C. overnight over desiccant. Abeta film was then resolubilised in 100% DMSO and further diluted (1/25) in Ham's F12 medium. Blanks were prepared by adding equal amounts of DMSO to Ham's F12 medium. Abeta and Blank solutions were incubated overnight at 4° C.

The solution was centrifuged at 14.000×g for 10 min at 4° C. and supernatants were transferred to fresh tubes and protein concentration determined by NanoDrop®.

Cell Treatment.

At day in-vitro 21 primary rat hippocampal neurons were treated with equal volume of Blank/ADDL solution amounting to 0 and 1000 nM ADDL. Cultures were kept at 37° C. 5% CO2 for 24 h before PFA fixation. Viability was assessed using the Live-Dead assay from Thermo Fisher Catalog number: L3224.

Fixation.

Neurons were fixed in 4% PFA/Sucrose for 10 min at RT. Cells were permeabilized using a buffer containing 0.1% Triton-X/0.1% NaCit/PBS. After washing, the coverslips containing neurons were inverted onto a drop of mounting medium (H1000, Vector Laboratories) (w/o DAPI), dried at RT and sealed off.

Example 14—Ex-Vivo Inhibition of VGCC Activity

Figure 5:
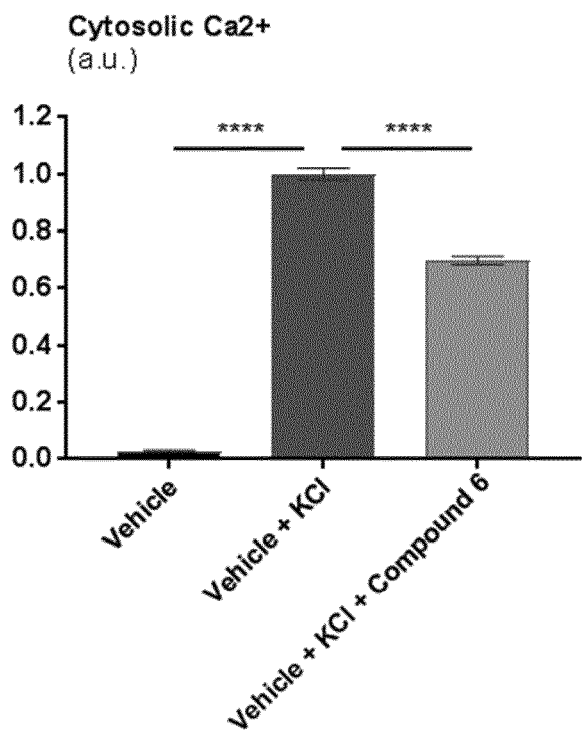
FIG. 5 represents a graph plotting cytosolic $Ca^{2+}$ levels in primary neurons after depolarization with 45 mM KCl of in the presence of vehicle or exemplary Compound 6. **** indicate $p<0.0001$.

Compound 6 was tested for its ability to inhibit VGCC activity in primary neurons. Neurons from mouse embryos were harvested and cultured using standard methods (such as used in Schlager et al., 2014. Cell reports, 8(5), pp. 1248-56). To stimulate VGCC activity, neurons were depolarized using 45 mM KCl and incubated with vehicle or compound at a concentration of 1.5 µm. Calcium influx was measured using fluorescent cytosolic $Ca^{2+}$ detection reagent Fura2. FIG. 5 shows that in compound treated neurons the $Ca^{2+}$ influx upon KCl depolarization was significantly reduced indicating that the compound inhibits VGCC activity.

Detailed Methods.

Changes in cytosolic $Ca^{2+}$ concentrations were measured after loading the cells with Fura-2 AM (Sigma-Aldrich), a cell permeable fluorescent probe for $Ca^{2+}$. Briefly, Fura-2-AM was dissolved in DMSO plus 20% Pluronic Acid (F-127) (Invitrogen) in a 1:1 ratio and diluted in medium to a final concentration of 0.5 µM. Probenecid (Sigma-Aldrich) was added to this loading medium at a final concentration of 2.5 mM. Then, culture medium was replaced by loading medium and after incubation for 1 hour at 37° C., cells were washed twice and replaced with HBSS (Gibco) supplemented with 0.2% FBS and 0.02M HEPES. Next, changes in cytosolic calcium were measured using a FlexStation 3 microplate reader (Molecular Devices) and quantified ratiometric, by calculating changes in the amount of cytosolic $Ca^{2+}$ bound Fura-2 (fluorescence intensity at 340 nm) relative to the amount of $Ca^{2+}$ unbound Fura-2 (fluorescence intensity at 380 nm). Data was processed in SoftMax Pro 5.4.6 software (Molecular Devices).

Example 15—In Vivo Inhibition of TAU-Instigated Pathologies

Transgenic human 5 month old APP*PS1 mice (The Journal of Neuroscience, Sep. 1, 2000, 20(17):6452-6458) were treated daily subcutaneously with 20 mg/kg Compound 6 for 2 weeks.

Figure 6:
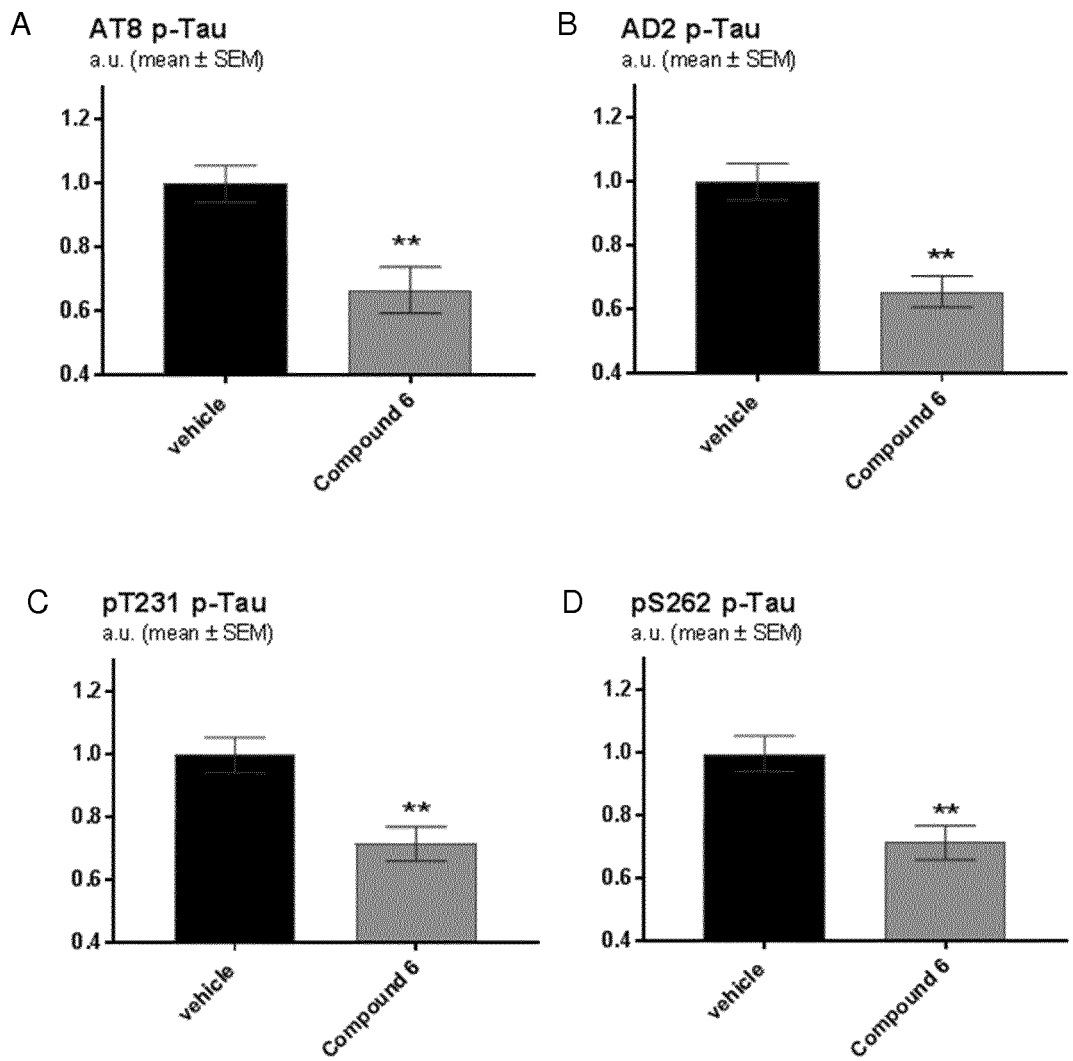
FIG. 6 represents graphs plotting quantifications of pathologically phosphorylated TAU species determined by Western blots of brain extracts from transgenic APP mice treated with vehicle or with exemplary Compound 6. The graphs depict the mean normalized TAU signals±SEM. ** indicate $p<0.01$ relative to vehicle treated animals. The TAU signals were obtained by using antibodies directed against.

At the end of the treatment period, mice were sacrificed and the corresponding brains were used for biochemical analysis. Western analysis of brain extracts using phospho-TAU specific antibodies showed that compared to vehicle treated mice, Compound 6 more effectively reduced TAU phosphorylation, demonstrating an in-vivo lowering effect of pathological TAU species in brain by compound 6 (FIG. 6).

Example 16—In-Vivo Effects on Cognition in a Mouse Model of Alzheimer's Disease Transgenic human of 4 months of age APP mice (THE JOURNAL OF BIOLOGICAL CHEMISTRY Vol. 274, No. 10, Issue of March 5, pp. 6483-6492, 1999) were treated subcutaneously, daily for 8 weeks with Compound 6 at 20 mg/kg. Cognition was assessed using the Morris Water Maze test. During the training phase, which evaluates the learning performance, the mice had over time a reduced search path compared to vehicle treated mice (FIG. 7, Section A). After the learning phase a probe test was conducted in which the platform was removed from the water bath to evaluate the spatial memory of the location of the platform. This test revealed (FIG. 7, Section B) a higher annulus crossing index score (which represents the number of swims over the platform site in the target area adjusted for swims over corresponding areas in other quadrants) than vehicle treated animals.

Both indices indicate that compound treated mice have improved cognitive performance almost identical to wild type controls compared to vehicle treated mice.

Example 17—Normalization of Neuronal Hyperactivation Ex-Vivo in a Mouse Model of Alzheimer's Disease Brain slices from wild type and tgAPP mice were incubated with DMSO or Compound 6. Neurons were stimulated with increasing currents and the frequency of action potentials (firing rate) was measured.

In tgAPP mice the frequency of action potentials at higher stimuli was higher. Incubation of the slices with exemplary Compound 6 significantly lowered the frequency towards wild type level (FIG. 8). These data demonstrates that in tgAPP mice neuronal activity is less or not restrained as observed in wild type mice and that the compound reduces this neuronal hyperactivity in tgAPP mice.

Acute Brain Slices:

Acute sagittal brain slices from WT or hAPP mice were prepared by decapitation of the mice after isoflurane anaesthesia. Brains were removed quickly and immersed during 3-4 min in ice-cold freshly prepared cutting artificial cerebrospinal fluid (cutting aCSF) containing (in mM) 214 sucrose, 2.5 KCl, 2 $CaCl2$), 2 $MgSO4$, 1.25 $NaH2PO2$, 26 $NaHCO3$ and 10 glucose and oxygenated with 95% $O2$/5% $CO2$. Sagittal 350 µm slices were generated using a vibratome (VT 1000S; Leica Microsystems) and were incubated in standard carboxygenated aCSF (in mM: 125 NaCl, 2.5 KCl, 2 $CaCl2$), 2 $MgSO4$, 1.25 $NaH2PO2$, 26 $NaHCO3$ and 10 glucose, osmolarity 305 mOsm) at 34° C. during 20 min. The incubation continued at room temperature (RT) for another hour before each slice was transferred to a submerged recording chamber and perfused continuously with carboxygenated aCSF.

Patch clamp recording of CA1 single action potential (sAP) and firing rate:

Somatic or dendritic (>200 µm from the soma) current-clamp recordings were performed at RT (24 to 28° C.) and slices were continuously perfused with carboxygenated standard aCSF, supplemented with control or test article REM0043039 at 2 µM. For whole-cell recordings, patch pipettes were filled with a solution containing (in mM) 140 K-gluconate, 5 NaCl, 2 $MgCl2$, 10 HEPES, 0.5 EGTA, 2 MgATP, 0.4 NaGTP, osmolarity 305, pH adjusted to 7.25 with KOH. The soma or dendrite of large CA1 pyramidal neurons were identified and patch-clamped after visual approach of the recording pipette using a combination of infrared light and differential interference contrast (DIC) optics. Patch electrodes had a resistance of around 5 and 14 MO when filled for somatic and dendritic recording, respectively. Recordings were terminated when the series resistances exceeded 40 MO. Signals were digitized and low-pass filtered at 10 kHz. The signal was amplified with an Axopatch 200B amplifier, digitized by a Digidata 155 interface and sampled with Clampex 10 (Molecular Devices, CA).

A single spike was elicited by injecting a 2 ms depolarizing current pulse (35 pA) and action potential (AP) parameters were at baseline and after 25 min vehicle or compound perfusion.

Dendritic firing rate of CA1 cells was recorded in response to hyperpolarizing and depolarizing steps (−0.4 to +0.45 nA, steps of 0.05 nA) after a 1 hr perfusion with vehicle or compound at 2 µM. The mean number of action potentials (firing rate) was plotted in function of current step intensity.

Example 18—Testing of Compounds in the Kainite Epilepsy Model

Compounds were tested in the rat kainite epilipsy model.

Pharmacological evaluation of the anti-epilepsy activity of compounds is performed in a kainic acid (KA) mouse model (Gröticke et al., 2008, Experimental Neurology, 213, pp. 71-83; Dietrich et al., August 2016, Conf Proc IEEE Eng Med Biol Soc., pp. 4005-4008). This model shows recurrent seizures after an initial KA-induced status epilepticus (SE) and a latent epileptogenic phase of 2-to-3 weeks.

KA is injected into the CA1 area of the dorsal hippocampus followed by a surgical ipsilateral implantation of bipolar electrodes for EEG recording. Based on the occurrence of a nonconvulsive SE induced by KA, mice are selected for enrolment into the study. A once or twice-a-week 1 hr video-EEG monitoring is used to record the hippocampal discharges (HPD) over time. Severity of behavioural (convulsive) seizures is rated according to Racine (Racine RJ, 1972, Electroencephalogr Clin Neurophysiol., 38(1):1-12).

Daily subcutaneous administration of compound (25 mg/kg) or vehicle treatment starts before or after the initial kainate induced SE. Compound treated mice show a decrease of more than 20% in kainate induced HPD and/or spontaneous seizures compared to vehicle treated mice.

Example 19—Compound Increases Afterhyperpolarization of Action Potentials

Improving the A-type potassium current has therapeutic potential for treating epilepsy as it reduced excitability of neurons.

Action potentials (AP) after electrical stimulation of mouse brain slices were analysed (FIG. 9). The afterhypolarization of AP's of slices incubated with Compound 6 was increased indicating that the compound facilitates neuronal repolarization to a resting state.

The experiment was performed as essentially described in Example 17.

Example 20—Use of the Calcium Dyshomeostasis Model of TAU.P301L Overexpressing Cells in the Screening Compounds of this Invention Compounds were tested to lower the elevated cytosolic $Ca^{2+}$ levels in the cell model of calcium dyshomeostasis (FIG. 1B) as described in example 10. Efficacy (potency) of the compounds was determined by testing compounds at different concentrations, ranging from non-effective to effective concentrations, for their ability to reduce the level of cytosolic $Ca^{2+}$ bound Fura-2 (fluorescence intensity at 340 nm) relative to the amount of $Ca^{2+}$ unbound Fura-2 (fluorescence intensity at 380 nm).

Exemplary compounds of the present invention are shown in Table 2, with their chemical structure and their $EC_{50}$ value of lowering cytosolic $Ca^{2+}$ (expressed in µg/ml).

TABLE 2

| Compound | Structure | $EC_{50}$ (µg/ml) |
|---|---|---|
| 1 | 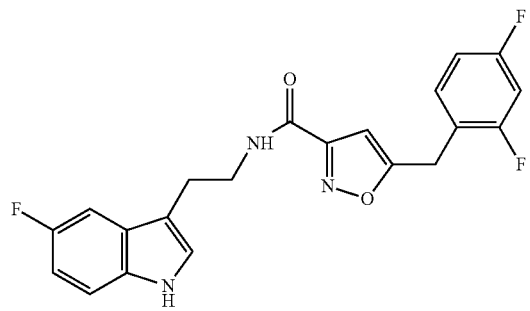 [SMILES: O=C(NCCc1c[nH]c2ccc(F)cc12)c1cc(Cc2ccc(F)cc2F)on1] | 0.0010 |
| 2 | 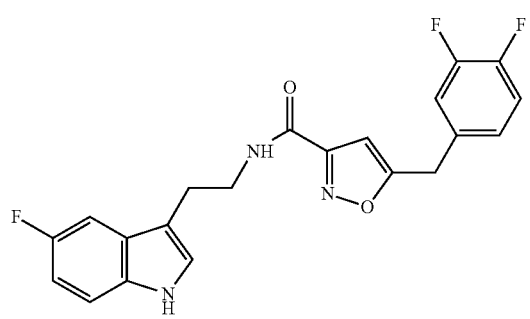 [SMILES: O=C(NCCc1c[nH]c2ccc(F)cc12)c1cc(Cc2ccc(F)c(F)c2)on1] | 0.0014 |

TABLE 2-continued
| Compound | Structure | EC$_{50}$ (µg/ml) |
|---|---|---|
| 3 | 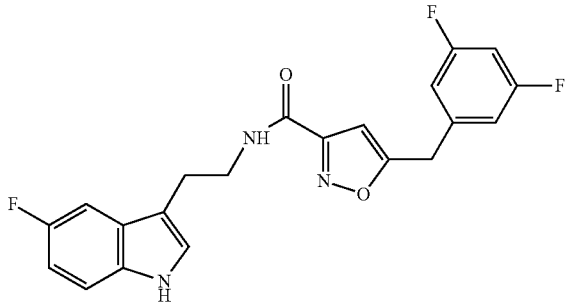 [SMILES: O=C(NCCc1c[nH]c2ccc(F)cc12)c1cc(Cc2cc(F)cc(F)c2)on1] | 0.0024 |
| 4 | 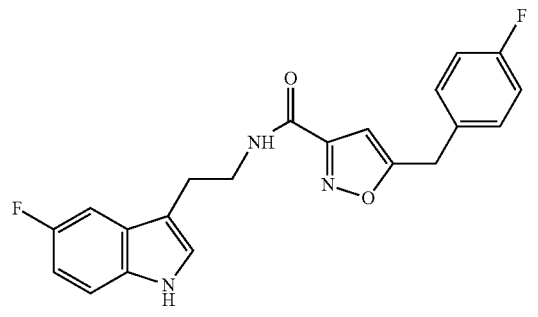 [SMILES: O=C(NCCc1c[nH]c2ccc(F)cc12)c1cc(Cc2ccc(F)cc2)on1] | 0.0035 |
| 5 | 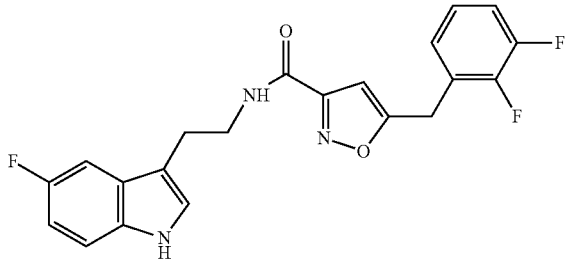 [SMILES: O=C(NCCc1c[nH]c2ccc(F)cc12)c1cc(Cc2cccc(F)c2F)on1] | 0.0071 |
| 6 | 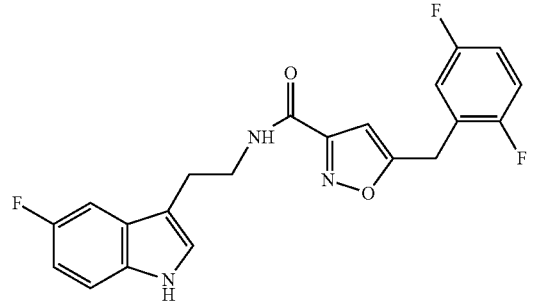 [SMILES: O=C(NCCc1c[nH]c2ccc(F)cc12)c1cc(Cc2cc(F)ccc2F)on1] | 0.0024 |
| 7 | 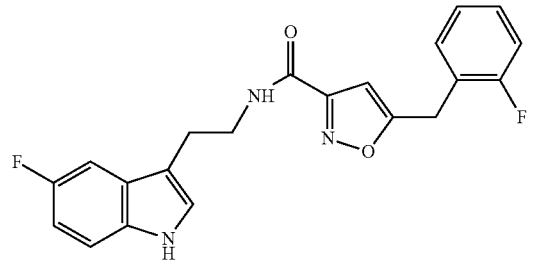 | 0.0047 |

Example 21—Use of the Ex-Vivo Model of KCl-Induced Calcium Influx in the Screening of Compounds for the Treatment of Epilepsy and Other Neurodegenerative Diseases Involving Calcium Dyshomeostasis Compounds were tested at 10 μM for their ability to inhibit $Ca^{2+}$ influx in primary neurons (FIG. 5) as described in Example 14. Primary neurons treated with vehicle in which no compound was dissolved was used as a no-effect control. The percentage (%) inhibition of $Ca^{2+}$ influx relative to vehicle treated neurons was calculated. Results are shown in Table 3.

TABLE 3

| Compound | % inhibition of cytosolic $Ca^{2+}$ influx |
| --- | --- |
| 1 | 43 |
| 2 | 48 |
| 3 | 42 |
| 4 | 39 |
| 5 | 42 |
| 6 | 43 |
| 7 | 56 |

The invention claimed is:

1. A compound of formula (I):

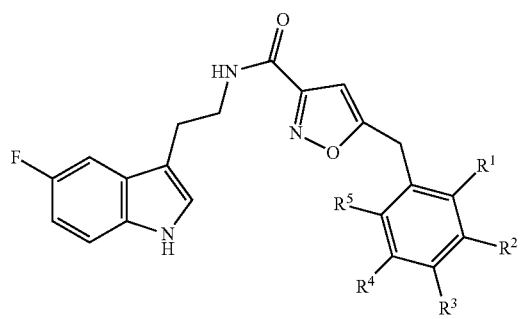

(I)

wherein,
$R^1$ is selected from the group consisting of hydrogen and F;
$R^2$ is selected from the group consisting of hydrogen and F;
$R^3$ is selected from the group consisting of hydrogen and F;
$R^4$ is selected from the group consisting of hydrogen and F;
$R^5$ is selected from the group consisting of hydrogen and F;
with the proviso that at least one of $R^1$, $R^2$, $R^3$, $R^4$ or $R^5$ is not hydrogen;
with the proviso that said compound of formula (I) is not N-[2-(5-fluoro-1H-indol-3-yl)ethyl]-5-[(3-fluorophenyl)methyl]isoxazole-3-carboxamide,
or a tautomer, a solvate, a hydrate, a salt or a prodrug thereof.

2. The compound according to claim 1, having any one of formula (II), (III), (IV), (V) or (VI)

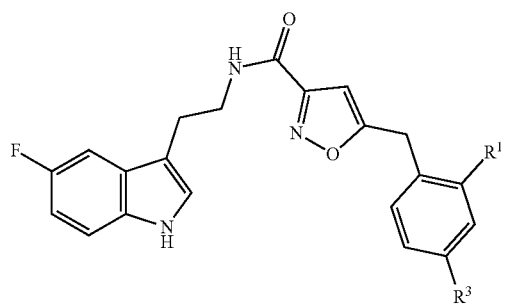

(II)

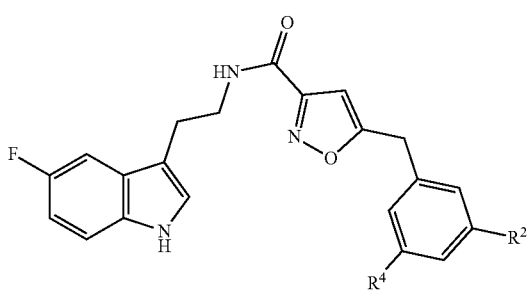

(III)

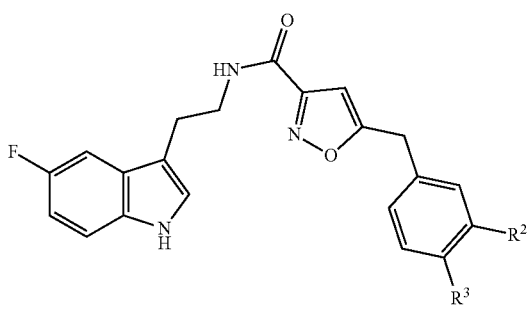

(IV)

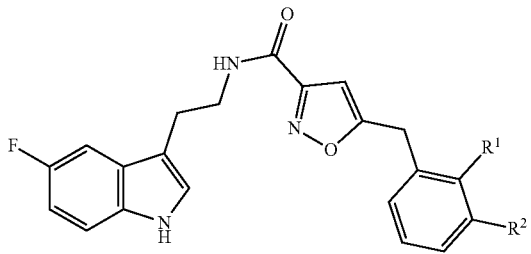

(V)

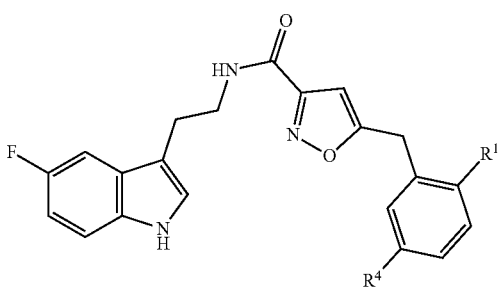

(VI)

wherein $R^1$, $R^2$, $R^3$ and $R^4$ have the same meaning as defined in claim 1.

3. The compound according to claim 1 or 2, wherein $R^2$, $R^3$, $R^4$ and $R^5$ are hydrogen; and wherein $R^1$ is F.

43

4. The compound according to claim 1 or 2, wherein $R^1$, $R^2$, $R^4$ and $R^5$ are hydrogen; and $R^3$ is F.

5. The compound according to claim 1 or 2, wherein $R^2$, $R^4$ and $R^5$ are hydrogen; and $R^1$ and $R^3$ are independently selected from the group consisting of hydrogen and F.

6. The compound according to claim 1 or 2, wherein $R^1$, $R^4$ and $R^5$ are hydrogen; and $R^2$ and $R^3$ are independently selected from the group consisting of hydrogen and F.

7. The compound according to claim 1 or 2, wherein $R^1$, $R^3$ and $R^5$ are hydrogen; and $R^2$ and $R^4$ are independently selected from the group consisting of hydrogen and F.

8. The compound according to claim 1 or 2, wherein $R^3$, $R^4$ and $R^5$ are hydrogen; and $R^1$ and $R^2$ are independently selected from the group consisting of hydrogen; and F.

9. The compound according to claim 1 or 2, wherein $R^2$, $R^3$ and $R^5$ are hydrogen; and $R^1$ and $R^4$ are independently selected from the group consisting of hydrogen and F.

10. The compound according to claim 1, selected from the group consisting of:
    5-[(2,4-difluorophenyl)methyl]-N-[2-(5-fluoro-1H-indol-3-yl)ethyl]isoxazole-3-carboxamide;
    N-[2-(5-fluoro-1H-indol-3-yl)ethyl]-5-[(4-fluorophenyl)methyl]isoxazole-3-carboxamide;
    5-[(2,3-difluorophenyl)methyl]-N-[2-(5-fluoro-1H-indol-3-yl)ethyl]isoxazole-3-carboxamide;
    5-[(2,5-difluorophenyl)methyl]-N-[2-(5-fluoro-1H-indol-3-yl)ethyl]isoxazole-3-carboxamide;
    N-[2-(5-fluoro-1H-indol-3-yl)ethyl]-5-[(2-fluorophenyl)methyl]isoxazole-3-carboxamide;
    5-[(3,4-difluorophenyl)methyl]-N-[2-(5-fluoro-1H-indol-3-yl)ethyl]isoxazole-3-carboxamide; and
    5-[(3,5-difluorophenyl)methyl]-N-[2-(5-fluoro-1H-indol-3-yl)ethyl]isoxazole-3-carboxamide.

11. A pharmaceutical composition comprising one or more pharmaceutically excipients and a therapeutically effective amount of a compound according to claim 1, or a tautomer, a solvate, a hydrate, a salt or a prodrug thereof.

12. The compound of claim 1, wherein:
    $R^1$ is selected from the group consisting of hydrogen and F;
    $R^2$ is selected from the group consisting of hydrogen and F;
    $R^3$ is selected from the group consisting of hydrogen and F;
    $R^4$ is selected from the group consisting of hydrogen and F;
    $R^5$ is selected from the group consisting of hydrogen and F;
    with the proviso that at least one of $R^1$, $R^2$, $R^3$, $R^4$ or $R^5$ is not hydrogen;
    with the proviso that said compound of formula (I) is not N-[2-(5-fluoro-1H-indol-3-yl)ethyl]-5-[(3-fluorophenyl)methyl]isoxazole-3-carboxamide,
    or a tautomer, a solvate, a hydrate or a salt thereof.

* * * * *